US 7,914,443 B2

(12) United States Patent
Uchimura et al.

(10) Patent No.: US 7,914,443 B2
(45) Date of Patent: Mar. 29, 2011

(54) ENDOSCOPE WITH NON-CONTACT SIGNAL TRANSMISSION AND RECEPTION

(75) Inventors: Sumihiro Uchimura, Sagamihara (JP); Akira Taniguchi, Hachioji (JP); Fumiyuki Onoda, Tama (JP); Toshiaki Noguchi, Tachikawa (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1167 days.

(21) Appl. No.: 11/599,562

(22) Filed: Nov. 14, 2006

(65) Prior Publication Data

US 2007/0060789 A1    Mar. 15, 2007

Related U.S. Application Data

(63) Continuation of application No. PCT/JP2005/008801, filed on May 13, 2005.

(30) Foreign Application Priority Data

May 14, 2004  (JP) .................................. 2004-145695
May 14, 2004  (JP) .................................. 2004-145704

(51) Int. Cl.
*A61B 1/04* (2006.01)
*A61B 1/012* (2006.01)
(52) U.S. Cl. ......... 600/110; 600/132; 600/134; 600/136
(58) Field of Classification Search .................. 600/110, 600/132, 134, 136
See application file for complete search history.

(56) References Cited

U.S. PATENT DOCUMENTS

| 3,611,255 | A | * | 10/1971 | Shroyer .................... 439/282 |
| 3,808,580 | A | * | 4/1974 | Johnson .................... 439/321 |
| 4,325,606 | A | * | 4/1982 | Ikuno et al. .................... 385/76 |
| 4,609,247 | A | * | 9/1986 | Annoot .................... 439/591 |
| 5,671,738 | A | * | 9/1997 | Thornberg .................... 600/407 |
| 5,702,345 | A | * | 12/1997 | Wood et al. .................... 600/109 |
| 5,716,323 | A | * | 2/1998 | Lee .................... 600/134 |
| 5,913,817 | A | * | 6/1999 | Lee .................... 600/134 |
| 6,022,237 | A | * | 2/2000 | Esh .................... 439/348 |
| 6,099,465 | A | * | 8/2000 | Inoue .................... 600/134 |
| 2001/0051766 | A1 | * | 12/2001 | Gazdzinski .................... 600/309 |
| 2003/0069475 | A1 | | 4/2003 | Banik et al. |
| 2004/0104999 | A1 | * | 6/2004 | Okada .................... 348/65 |
| 2006/0293562 | A1 | * | 12/2006 | Uchimura et al. .................... 600/110 |

FOREIGN PATENT DOCUMENTS

| GB | 2 352 922 A | 2/2001 |
| JP | 10-262908 | 10/1998 |
| JP | 10-295635 | 11/1998 |
| JP | 2000-157486 | 6/2000 |
| JP | 2001-008885 | 1/2001 |

* cited by examiner

Primary Examiner — John P Leubecker
(74) Attorney, Agent, or Firm — Scully, Scott, Murphy and Presser, P.C.

(57) ABSTRACT

An endoscope is provided that can reduce examination costs by realizing commonality of an operating unit by making an inserting unit and the operating unit attachable/detachable with respect to each other to enable the exchange of inserting units. The endoscope of this invention includes an operating unit, an inserting unit that can be detachably connected to the operating unit, and transmission and reception coils provided in the operating unit and the inserting unit, respectively, for sending and receiving signals in a non-contact manner between the operating unit and the inserting unit when the inserting unit is connected to the operating unit.

26 Claims, 32 Drawing Sheets

ENDOSCOPE WITH NON-CONTACT SIGNAL TRANSMISSION AND RECEPTION

CROSS REFERENCE TO RELATED APPLICATION

This application is a continuation application of PCT/JP2005/008801 filed on May 13, 2005 and claims benefit of Japanese Applications No. 2004-145695 filed in Japan on May 14, 2004 and No. 2004-145704 filed in Japan on May 14, 2004, the entire contents of each of which are incorporated herein by their reference.

BACKGROUND OF THE INVENTION

1. Field of the Invention

The present invention relates to an endoscope that is inserted into a body cavity or the like to perform endoscopy or the like.

2. Description of the Prior Art

Endoscope devices have been widely used in the field of medical treatment and the like. In particular, an endoscope device in the medical treatment field is mainly used for the purpose of enabling a technician to carry out treatment such as in vivo examination or observation of a patient.

As an endoscope used to perform treatment such as in vivo examination or observation of a patient, for example, an endoscope disclosed in Japanese Patent Laid-Open No. 2000-157486 is widely known. The endoscope disclosed in the aforementioned document chiefly comprises an inserting unit and an operating unit, and these are configured in an integrated manner.

SUMMARY OF THE INVENTION

The endoscope according to the present invention comprises an operating unit; an inserting unit that is detachably connected to the operating unit; and signal transmission and reception sections that are respectively provided in the operating unit and the inserting unit, and perform sending and receiving of signals between the operating unit and the inserting unit in a non-contact manner when the inserting unit is connected to the operating unit.

DETAILED DESCRIPTION OF THE PREFERRED EMBODIMENTS

Hereunder, embodiments of the present invention are described with reference to the drawings.

First Embodiment

Figure 1:
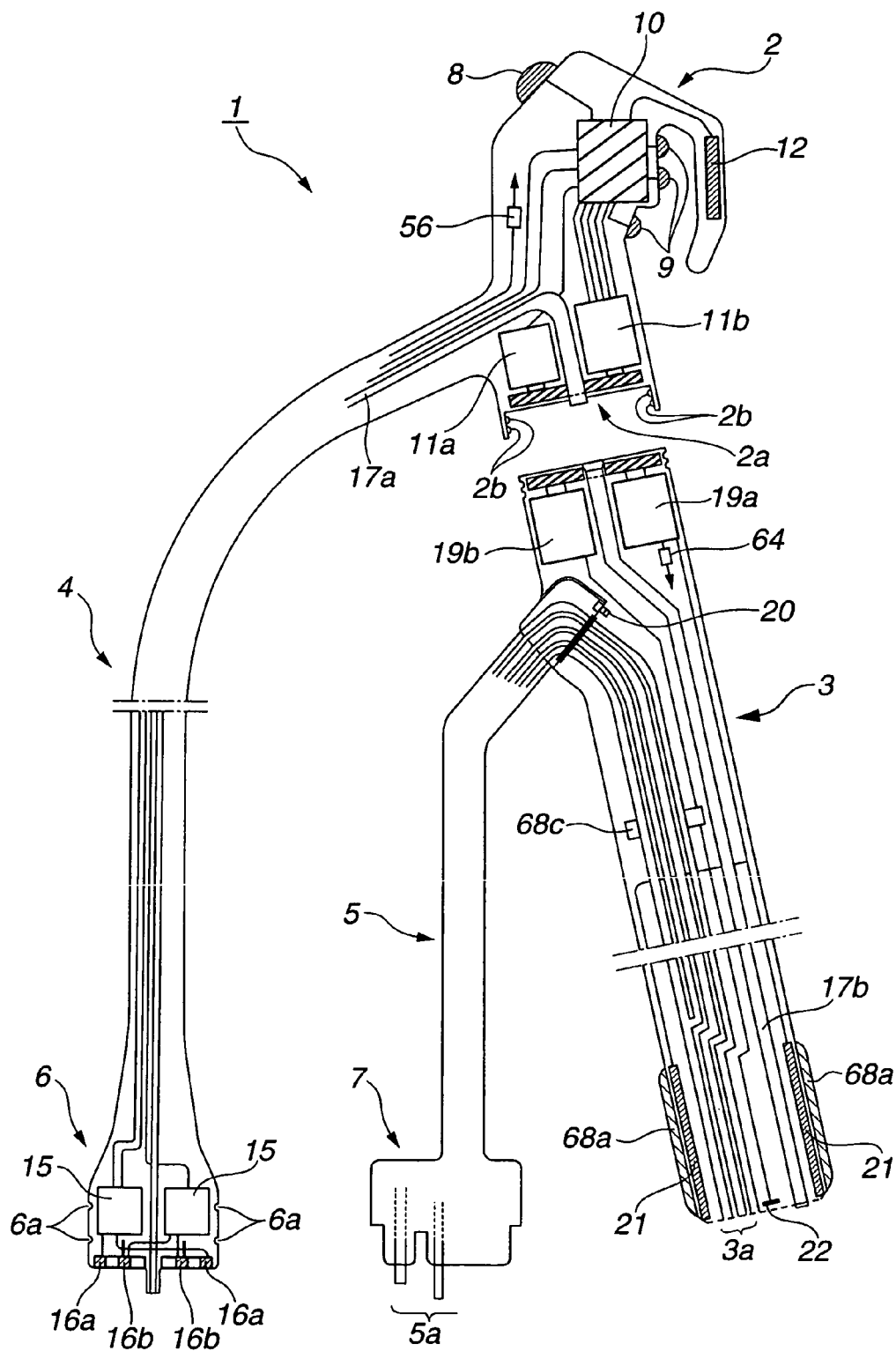
FIG. 1 is a view for describing the structure of an endoscope according to a first embodiment.
Figure 2:
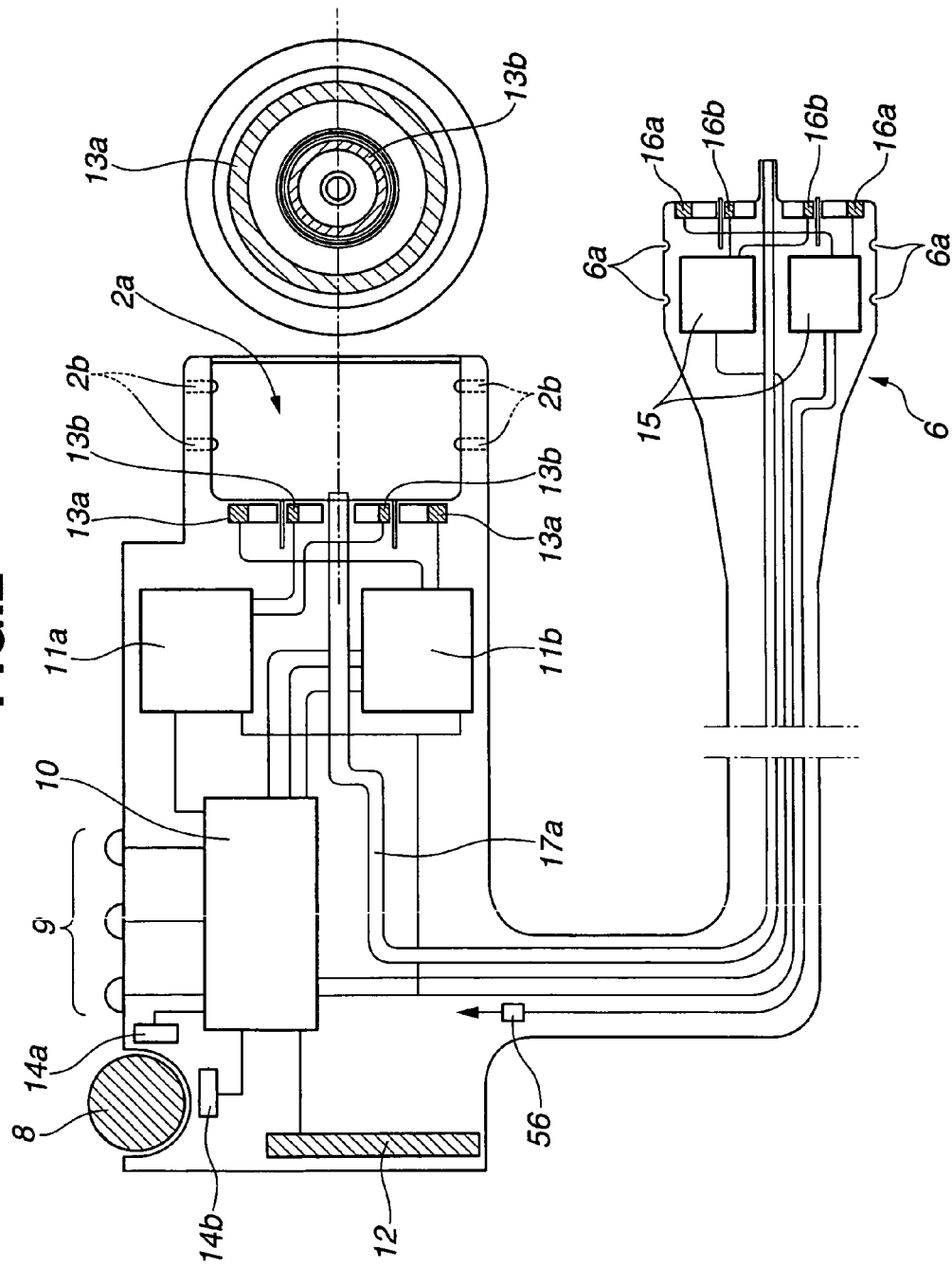
FIG. 2 is a view for describing the structure of an operating unit of the endoscope according to the first embodiment.
Figure 3:
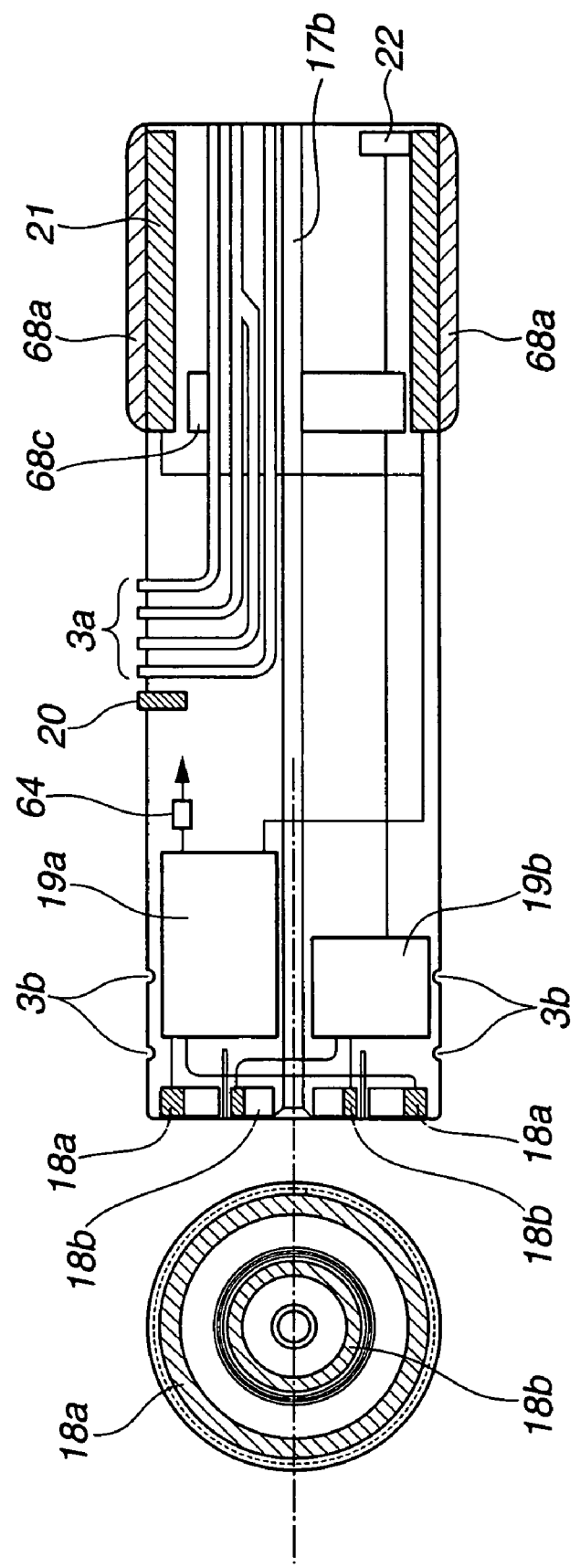
FIG. 3 is a view for describing the structure of an inserting unit of the endoscope according to the first embodiment.
Figure 4:
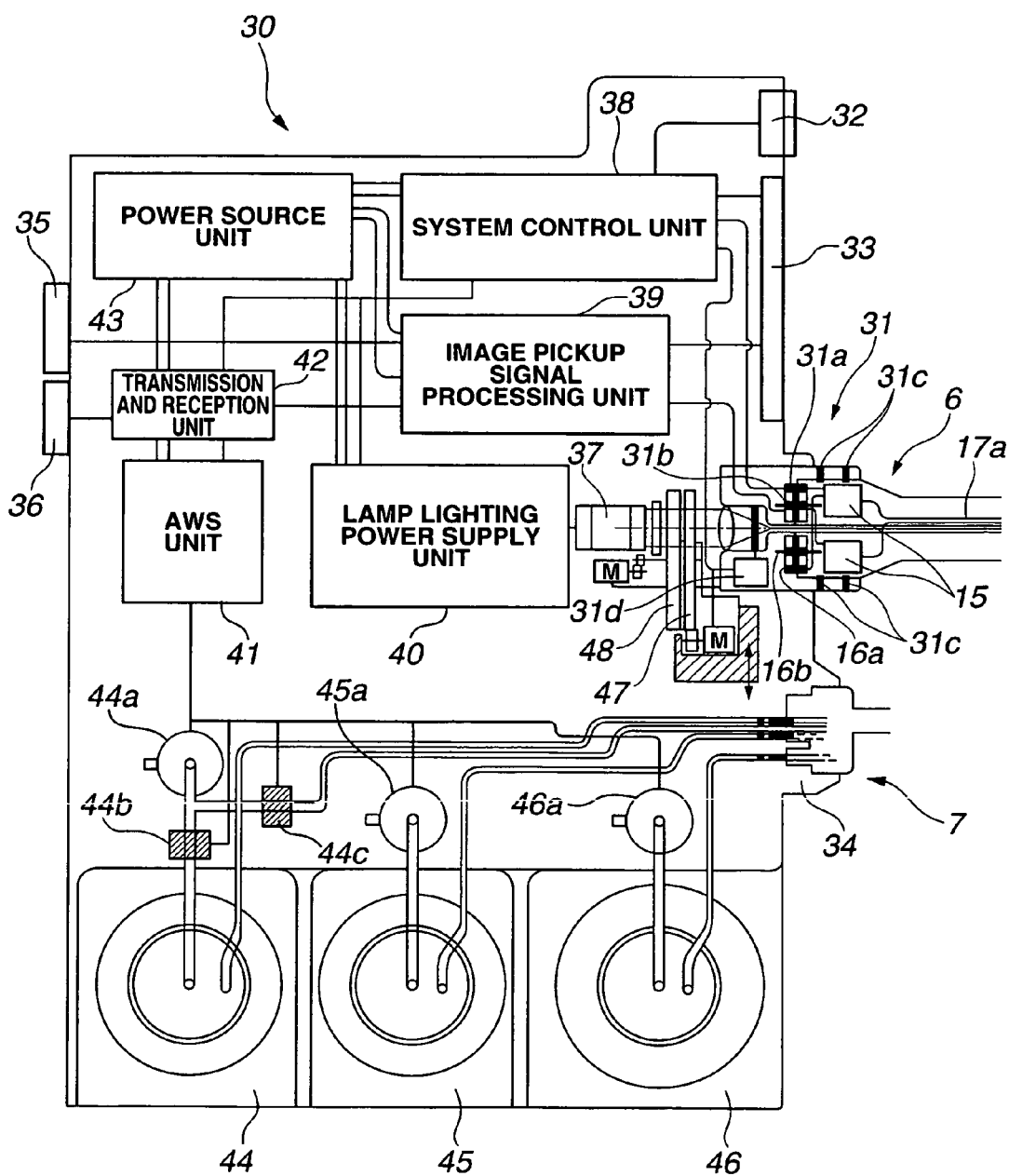
FIG. 4 is a schematic configuration diagram of an endoscope system controlling apparatus to which a scope connector of the endoscope according to the first embodiment is connected.
Figure 5:
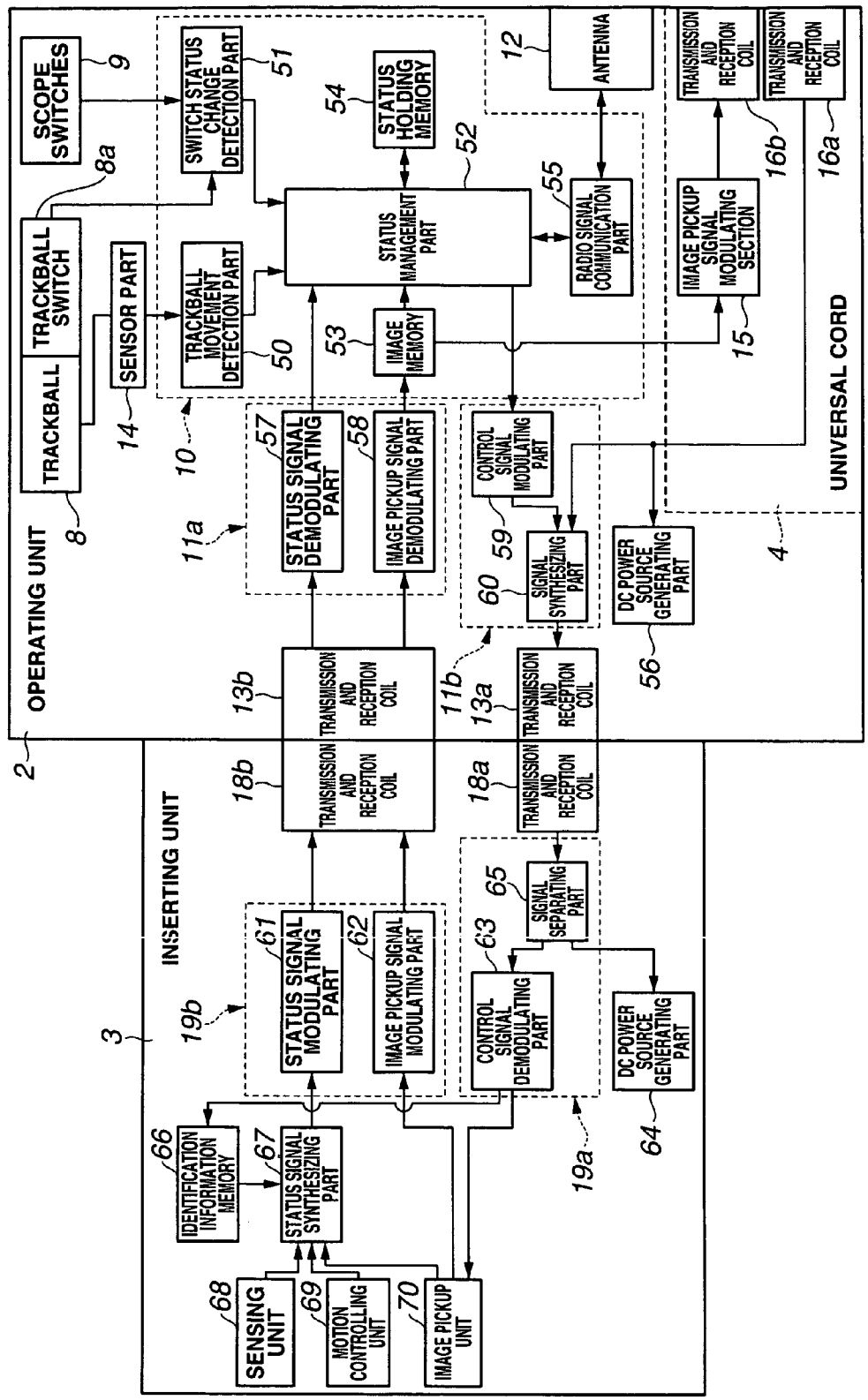
FIG. 5 is a block diagram showing the internal configuration of the operating unit and the inserting unit of the endoscope according to the first embodiment.
Figure 6:
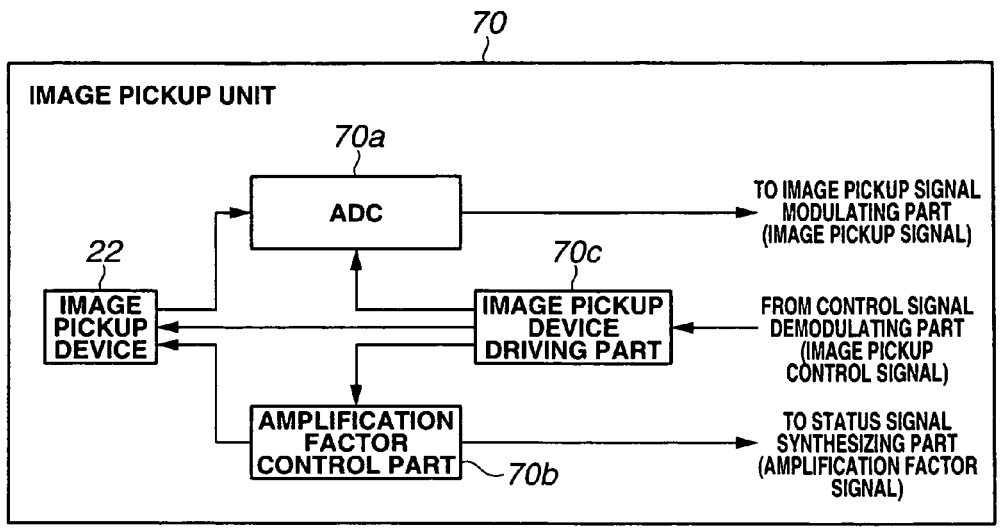
FIG. 6 is a block diagram showing the internal configuration of an image pickup unit that is provided in the inserting unit of the endoscope according to the first embodiment.
Figure 7:
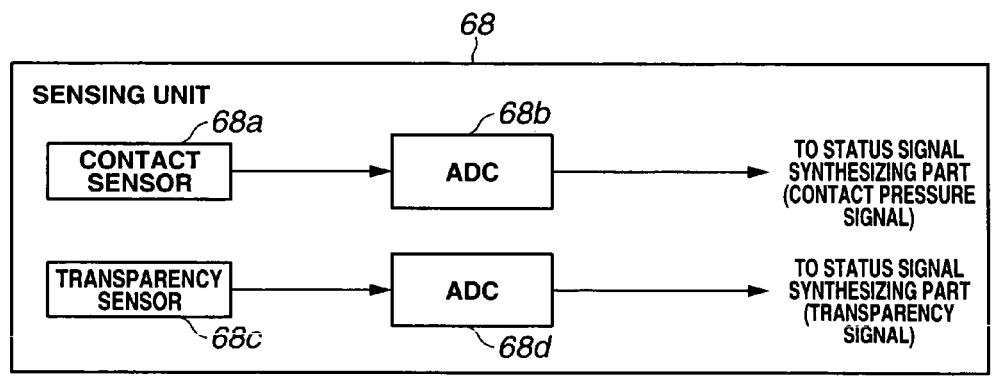
FIG. 7 is a block diagram showing the internal configuration of a sensing unit that is provided in the inserting unit of the endoscope according to the first embodiment.
Figure 8:
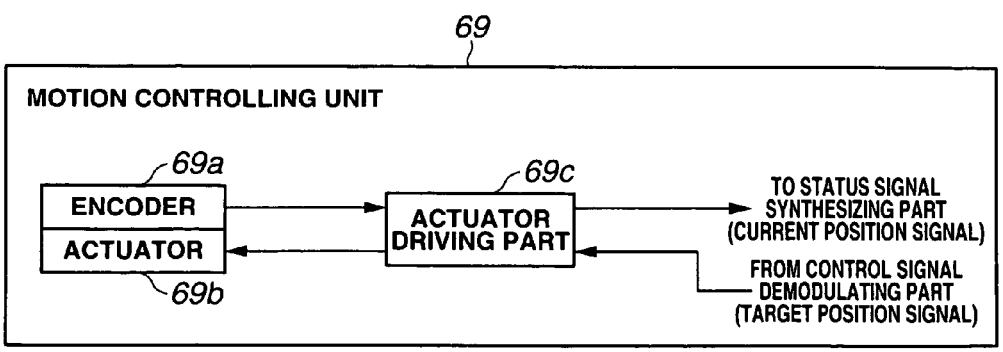
FIG. 8 is a block diagram showing the internal configuration of a motion controlling unit that is provided in the inserting unit of the endoscope according to the first embodiment.
Figure 9:
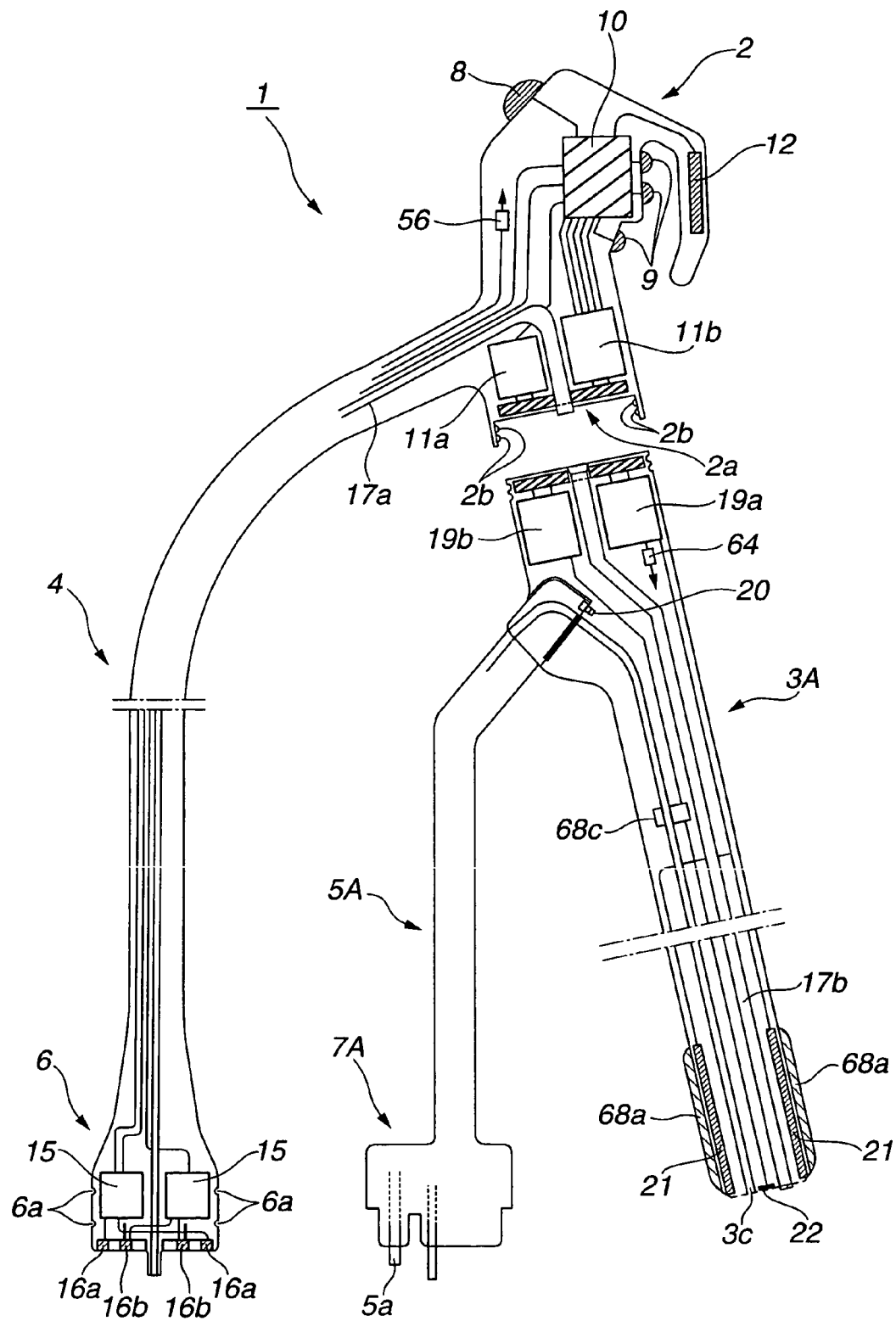
FIG. 9 is a view for describing a configuration illustrating a first modification example of the endoscope according to the first embodiment.
Figure 10:
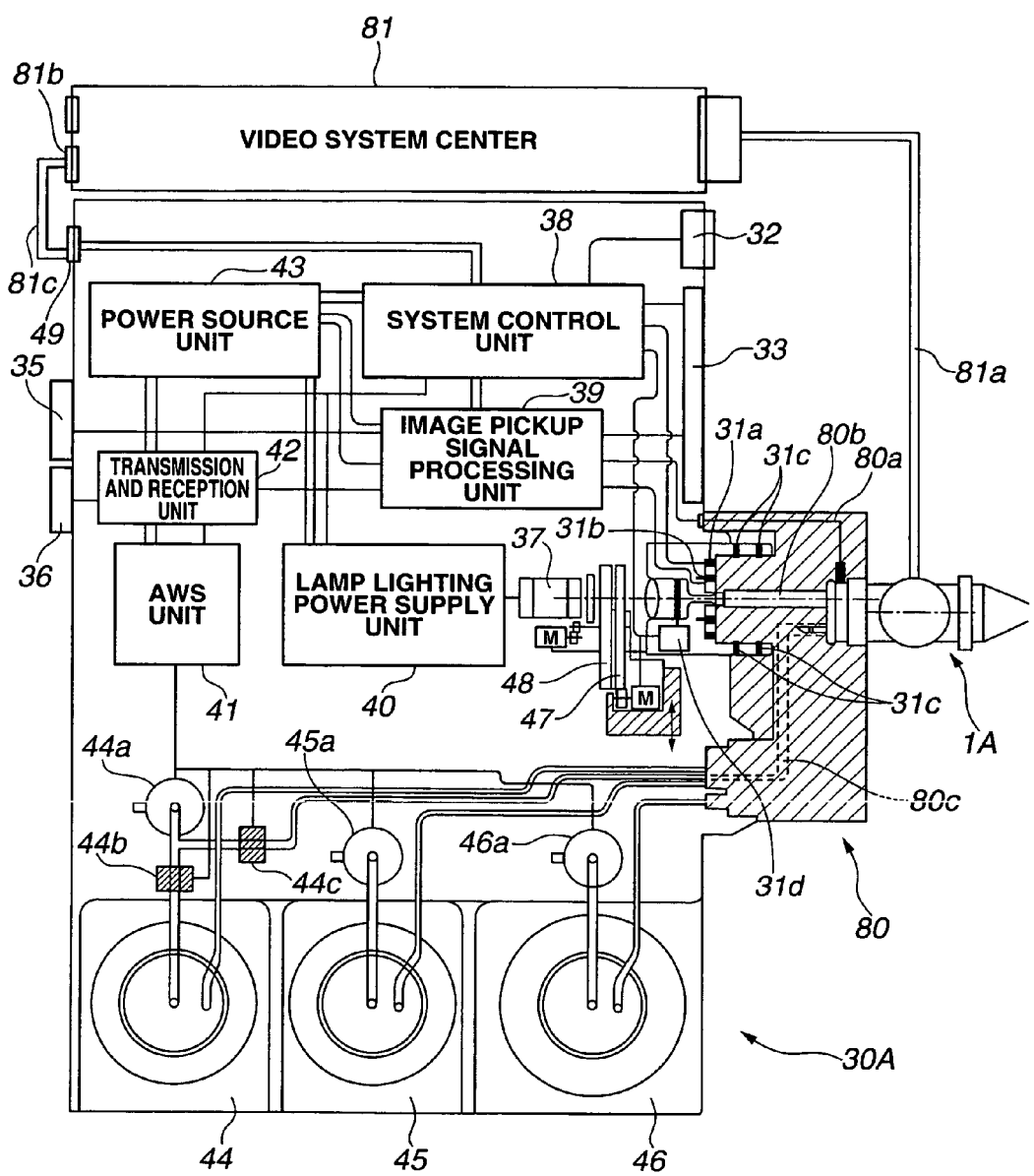
FIG. 10 is a view for describing a configuration in a case where a conventional endoscope is connected to the endoscope system controlling apparatus according to the first embodiment.
Figure 11:
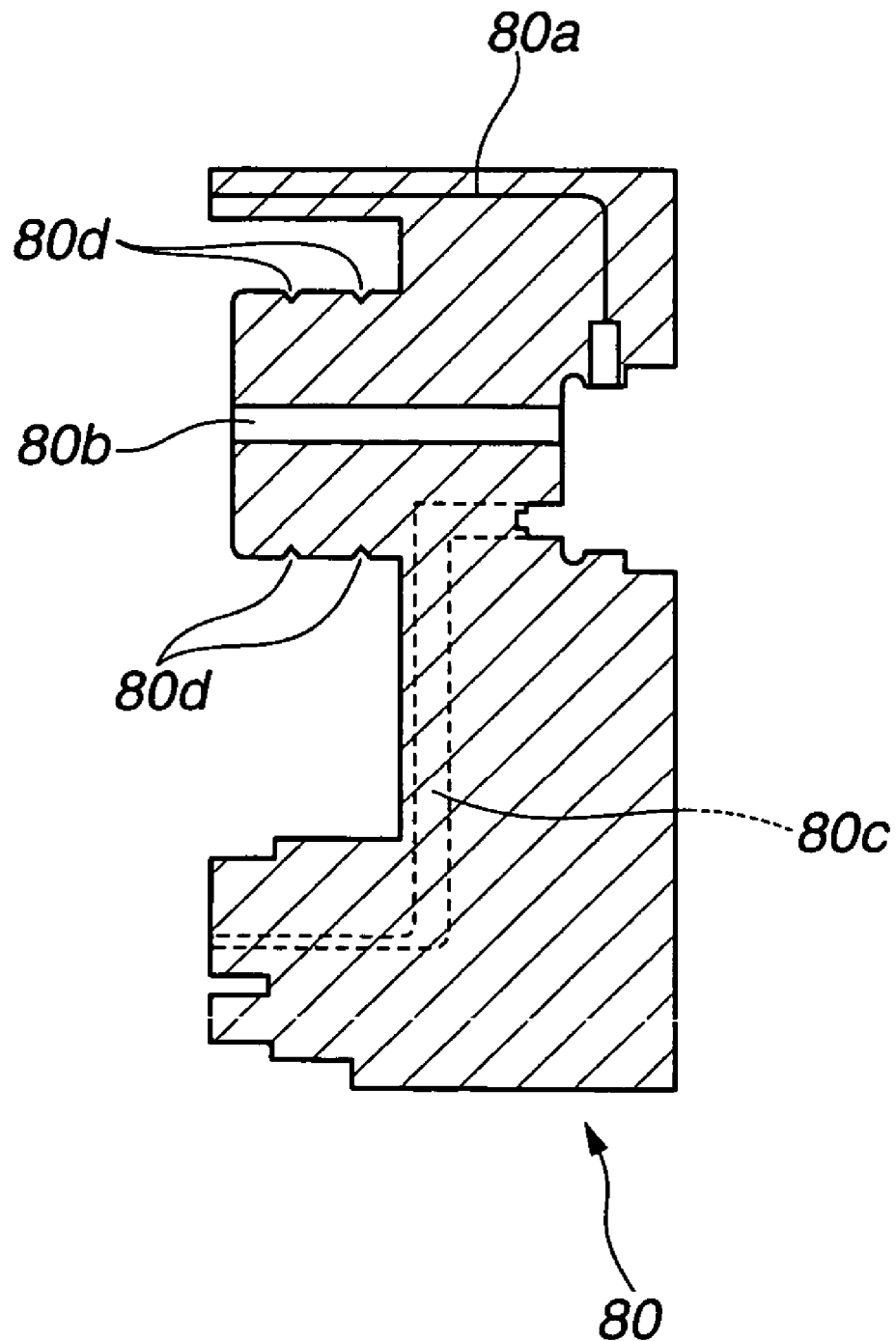
FIG. 11 is a sectional view of an adapter that is used when connecting a conventional endoscope to the endoscope system controlling apparatus according to the first embodiment.

FIGS. 1 to 11 relate to the first embodiment of this invention. FIG. 1 is a view for describing the structure of an endoscope according to the present embodiment. FIG. 2 is a view for describing the structure of an operating unit of the endoscope according to this embodiment. FIG. 3 is a view for describing the structure of an inserting unit of the endoscope according to this embodiment. FIG. 4 is a schematic configuration diagram of an endoscope system controlling apparatus to which a scope connector of the endoscope according to this embodiment is connected. FIG. 5 is a block diagram showing the internal configuration of the operating unit and the inserting unit of the endoscope according to this embodiment. FIG. 6 is a block diagram showing the internal configuration of an image pickup unit that is provided in the inserting unit of the endoscope according to this embodiment. FIG. 7 is a block diagram showing the internal configuration of a sensing unit that is provided in the inserting unit of the endoscope according to this embodiment. FIG. 8 is a block diagram showing the internal configuration of a motion controlling unit that is provided in the inserting unit of the endoscope according to this embodiment. FIG. 9 is a view for describing a configuration that illustrates a first modification example of the endoscope according to this embodiment. FIG. 10 is a view for describing a configuration in a case where a conventional endoscope is connected to the endoscope system controlling apparatus according to this embodiment. FIG. 11 is a sectional view of an adapter that is used when connecting a conventional endoscope to the endoscope system controlling apparatus according to this embodiment.

An endoscope 1 has an operating unit 2 and an inserting unit 3. The operating unit 2 has a connector portion 2a that is formed at the end of the operating unit 2 as an operating unit side engaging portion and, as shown in FIG. 2, ball plungers 2b are provided as protrusions on the inner peripheral surface of the connector portion 2a. As shown in FIG. 3, on the outer peripheral surface of the inserting unit 3, peripheral grooves 3b that are concave portions are provided as an inserting unit side engaging portion. The ball plungers 2b are configured so as to be capable of engaging with the peripheral grooves 3b. Through this structure, the operating unit 2 and the inserting unit 3 are detachable and rotatable with respect to each other. In this embodiment, when the ball plungers 2b and the peripheral grooves 3b are engaged, transmission and reception coils 13a and 13b, described later, that are provided in the operating unit 2 and transmission and reception coils 18a and 18b, described later, that are provided in the inserting unit 3 are disposed at positions that are physically separated.

A universal cord 4 extends from the operating unit 2, and a tube unit 5 extends from the inserting unit 3. A scope connector 6 is provided at a tip part of the universal cord 4, and peripheral grooves 6a are provided on the outer peripheral surface of the scope connector 6. By means of the peripheral grooves 6a, the scope connector 6 has a structure that is detachable in a non-contact manner with respect to an endoscope system controlling apparatus 30, described later. A tube connector 7 is provided at the tip part of the tube unit 5, and has a structure that is attachable/detachable with respect to the endoscope system controlling apparatus 30 that is described later. Further, various conduits 5a for performing air supply and water supply and the like are provided inside the tube unit 5. In addition, the tube unit 5 has a structure that is attachable/detachable with respect to the inserting unit 3.

A trackball 8 and scope switches 9 are provided on the outer surface of the operating unit 2. The trackball 8 is formed in the shape of a sphere, and a technician can perform various operations and the like such as a bending movement or a settings change by rotating or pressing the trackball 8. A technician can also perform various operations such as supplying air or supplying water by pressing the scope switches 9.

As shown in FIG. 2, the operating unit 2 internally comprises a control circuit 10, transmission and reception circuits 11a and 11b, an antenna 12, transmission and reception coils 13a and 13b, sensors 14a and 14b, and a light guide fiber 17a.

As shown in FIG. 3, the inserting unit 3 internally comprises various conduits 3a that include a plurality of conduits, a light guide fiber 17b, transmission and reception coils 18a and 18b, transmission and reception circuits 19a and 19b, a leak detection mouth 20, an angle member 21, an image pickup device 22, contact sensors 68a that are described later, and a transparency sensor 68c that is described later. In addition to the aforementioned parts, a motion controlling unit 69 and the like are also provided in the inserting unit 3, however these parts are not shown in FIG. 3 and a detailed description of these parts including their operation is described later.

The various conduits 3a are configured so as to communicate with the various conduits 5a that are provided within the tube unit 5 when the tube unit 5 is connected to the inserting unit 3, and by means of this configuration air supply and water supply and the like can be performed to the interior of the body of the examinee.

The angle member 21 is provided at a tip part of the inserting unit 3, and by operation of the trackball 8 by a technician, the tip part of the inserting unit 3 can be bent in accordance with the control contents of the motion controlling unit 69 that is described later.

The control circuit 10 receives as signals the contents of operations performed by the technician from the scope switches 9 and the sensors 14a and 14b that are connected to the trackball 8. The control circuit 10 sends control signals to each part based on the state of these signals. The control circuit 10 is also connected to the antenna 12, and sends and receives control signals to and from the endoscope system controlling apparatus 30, as described later, via the antenna 12.

The control circuit 10 is connected to the transmission and reception circuits 11a and 11b. When the inserting unit 3 is connected to the operating unit 2, the control circuit 10 sends control signals via the transmission and reception circuit 11b and the transmission and reception coil 13a to the transmission and reception coil 18a that is provided in the inserting unit 3. When the inserting unit 3 is connected to the operating unit 2, the control circuit 10 receives an image pickup signal and a control signal as a video signal that are sent from the transmission and reception coil 18b provided in the inserting unit 3 via the transmission and reception coil 13b and the transmission and reception circuit 11a. The control circuit 10 sends the image pickup signal and the control signal that were received to an image pickup signal modulating part 15 that is provided inside the scope connector 6. When the universal cord 4 is connected to the endoscope system controlling apparatus 30, after performing frequency modulation of the image pickup signal and the control signal, the image pickup signal modulating part 15 sends the image pickup signal and the control signal to the endoscope system controlling apparatus 30 via a transmission and reception coil 16a.

Since the sectional form of the transmission and reception coils 13a and 13b that serve as a signal transmission and reception section is annular, when the inserting unit 3 is connected to the operating unit 2, sending and receiving of various signals can be performed in a non-contact manner by electromagnetic induction with the transmission and reception coils 18a and 18b that serve as a signal transmission and reception section and have a similar structure. Further, since the sectional form of transmission and reception coils 16a and 16b is also annular, similarly to the transmission and reception coils 13a and 13b, when the universal cord 4 is connected to the endoscope system controlling apparatus 30, sending and receiving of various signals can be performed in a non-contact manner by electromagnetic induction with the transmission and reception coils 31a and 31b that are provided in the endoscope system controlling apparatus 30.

The power required to drive each part provided in the operating unit 2 and the inserting unit 3 is supplied to the operating unit 2 and the inserting unit 3 as a power signal that was encoded at the endoscope system controlling apparatus 30. More specifically, a power signal sent from the endoscope system controlling apparatus 30 is sent in a non-contact manner from the transmission and reception coil 31a to the transmission and reception coil 16a, and thereafter sent to the transmission and reception coil 13a via the transmission and reception circuit 11b. Upon receiving the power signal, the transmission and reception coil 13a sends the power signal in a non-contact manner to the transmission and reception coil 18a by electromagnetic induction. The transmission and reception coil 18a receives the power signal in a non-contact manner by electromagnetic induction. The transmission and reception coil 18a then sends the received power signal to a DC power source generating part 64 that is described later.

As shown in FIG. 2, a light guide fiber 17a is provided as a first light guide part within the operating unit 2 and the universal cord 4, and as shown in FIG. 3, a light guide fiber 17b is provided as a second light guide part within the inserting unit 3. The light guide fiber 17a and the light guide fiber 17b are configured such that they communicate when the inserting unit 3 is connected to the operating unit 2, and by means of this configuration an illumination light supplied from the endoscope system controlling apparatus 30 is irradiated inside the body of an examinee from the tip part of the inserting unit 3.

The leak detection mouth 20 is provided in the vicinity of the various conduits 3a and is configured to be capable of detecting the occurrence of a leak in any of the various conduits 3a.

The transmission and reception circuit 19a receives a power signal and a control signal sent from the control circuit 10 via the transmission and reception coil 18a, and sends a power signal required for driving each part to the DC power source generating part 64 and sends a control signal for each part to the angle member 21, image pickup device 22 and the like. The transmission and reception circuit 19b receives a signal such as an image pickup signal from inside the body of an examinee that was photographed by the image pickup device 22, and sends the image pickup signal to the control circuit 10 via the transmission and reception coil 18b.

The internal configuration of the endoscope system controlling apparatus 30 to which the scope connector 6 and the tube connector 7 of the endoscope 1 of this embodiment are connected will now be described with reference to FIG. 4.

The endoscope system controlling apparatus 30 has a first multi-connector 31, a second multi-connector 32, a panel control unit 33, a tube connector connecting section 34, a video input/output section 35 and an antenna 36 on the outer surface of a case.

The first multi-connector 31 internally comprises transmission and reception coils 31a and 31b, ball plungers 31c and an aperture unit 31d.

Since the sectional form of the transmission and reception coils 31a and 31b is annular, when the universal cord 4 is connected to the endoscope system controlling apparatus 30, sending and receiving of various signals can be performed in a non-contact manner by electromagnetic induction with the transmission and reception coils 16a and 16b that have a similar structure. The ball plungers 31c are provided on the inner peripheral surface of the first multi-connector 31. The ball plungers 31c have a configuration that can engage with the peripheral grooves 6a, and by means of this configuration the universal cord 4 has a structure that is attachable/detachable with respect to the endoscope system controlling apparatus 30. The aperture unit 31d can adjust the strength of illumination light that is supplied from a lamp 37 as a light source.

The second multi-connector 32 is connected to a system control unit 38 inside the endoscope system controlling apparatus 30, and can connect various cables such as a serial cable on the outer surface of the endoscope system controlling apparatus 30. The panel control unit 33 has switches and the like for operating and controlling the endoscope system controlling apparatus 30.

The tube connector connecting section 34 has a structure that is attachable/detachable with respect to the tube connector 7. When the tube connector 7 is connected to the tube connector connecting section 34, the various conduits 5a communicate with the conduits provided inside the endoscope system controlling apparatus 30. The conduits provided inside the endoscope system controlling apparatus 30 are connected with a water supply bottle 44, an auxiliary water supply bottle 45 and a suction bottle 46. Partway along the conduit that is connected to the water supply bottle 44 are provided a first pump 44a, a first magnetic valve 44b and a second magnetic valve 44c. These parts operate together to regulate the amount of water supplied to a water supply conduit of the various conduits 5a. A second pump 45a is provided partway along the conduit connected to the auxiliary water supply bottle 45. The second pump 45a regulates the amount of water supplied to a water supply conduit of the various conduits 5a. Further, a third pump 46a is provided partway along the conduit connected to the suction bottle 46. The third pump 46a regulates the suction amount of in vivo body fluids that are drawn in by suction through a suction conduit of the various conduits 3a and a suction conduit of the various conduits 5a. The pumps and the magnetic valves are individually controlled based on the state of a control signal that is sent from an AWS (air supply/water supply/suction) unit 41.

The video input/output section 35 is connected to an image pickup signal processing unit 39 inside the endoscope system controlling apparatus 30, and can connect a monitor or the like. The antenna 36 is connected to a transmission and reception unit 42 inside the endoscope system controlling apparatus 30, and sends and receives control signals to and from an antenna 12 that is provided in the operating unit 2.

The system control unit 38 sends control signals to each part of the endoscope system controlling apparatus 30 to control each part. The image pickup signal processing unit 39 performs processing and the like of image pickup signals from inside the body of the examinee that were photographed by the image pickup device 22. A lamp lighting power supply unit 40 supplies to the lamp 37 the power that is necessary when the lamp 37 supplies an illumination light.

The lamp 37 supplies an illumination light for illuminating the interior of an examinee's body via the light guide fiber 17a and the light guide fiber 17b. An RGB filter 47 and a turret plate 48 are provided between the lamp 37 and the light guide fiber 17a, and enable color tone adjustment and the like. A power source unit 43 supplies power to the endoscope system 30, and also supplies the power required for driving various parts to the endoscope 1 as an encoded power signal.

Next, the internal configuration of the operating unit 2 and the inserting unit 3 of the endoscope 1 of this embodiment will be described referring mainly to FIG. 5.

The control circuit 10 provided inside the operating unit 2 has a trackball movement detection part 50, a switch status change detection part 51, a status management part 52, an image memory 53, a status holding memory 54, a radio signal communication part 55 and a DC power source generating part 56. In addition, as shown in FIG. 2, a sensor part 14 comprises a sensor 14a and a sensor 14b.

The transmission and reception circuit 11a provided inside the operating unit 2 comprises a status signal demodulating part 57 and an image pickup signal demodulating part 58, and performs demodulation of status signals and image pickup signals. The transmission and reception circuit 11b provided inside the operating unit 2 comprises a control signal modulating part 59 and a signal synthesizing part 60, and performs modulation of control signals and power signals.

The transmission and reception circuit 19a provided inside the inserting unit 3 comprises a control signal demodulating part 63 and a signal separating part 65, and performs separation and demodulation of control signals and power signals. The transmission and reception circuit 19b provided inside the inserting unit 3 comprises a status signal modulating part 61 and an image pickup signal modulating part 62, and modulates status signals and image pickup signals.

After detecting through the sensor part 14 that the trackball 8 was rotated by a technician, the trackball movement detection part 50 sends the detection contents as a signal to the status management part 52. After detecting that the trackball 8 was pressed by a technician or that the scope switches 9 were pressed or the like, the switch status change detection part 51 sends the detection contents as a signal to the status management part 52.

The image memory 53 can record image pickup signals of the interior of an examinee's body that were photographed by the image pickup unit 70 that has the image pickup device 22. The status holding memory 54 is configured, for example, as a non-volatile rewritable recording part in which model information of the endoscope 1 and information specific to individual devices and the like is recorded.

The status management part 52 has an unshown CPU (central processing unit) and the like, and controls each part of the operating unit 2 and the inserting unit 3. Based on the status of signals that are sent from the trackball movement detection part 50 and the switch status change detection part 51, more specifically, signals that are sent in accordance with a change in position of, or with the existence or non-existence of pressing of, the trackball 8 and the existence or non-existence of pressing of the scope switches 9, the status management part 52 sends signals for performing control and operation and the like, i.e. signals for controlling the amount of illumination light or for performing a bending movement and the like, to the radio signal communication part 55 and the control signal modulating part 59. Further, the status management part 52 receives as status signals the contact state of the tip part of the inserting unit 3 inside the body of the examinee and the contamination state of the various conduits 3a that is detected by a sensing unit 68 to be described later, as well as the bending amount of the inserting unit 3 that is detected by the motion controlling unit 69 and the amplification factor of the image pickup device 22 that is acquired by the image pickup unit 70. These units are provided in the inserting unit 3. Based on the status of the relevant signals and the contents of information stored in the status holding memory 54, the status management part 52 sends signals for performing control and the like to the radio signal communication part 55 and the control signal modulating part 59. The radio signal communication part 55 sends control signals that are received from the status management part 52 to the antenna 12. The status management part 52 also receives via the image pickup signal demodulating part 58 and the image memory 53, image pickup signals of the interior of the examinee's body that were photographed by the image pickup unit 70 that has the image pickup device 22.

After receiving a power signal that was sent to the operating unit 2 from the endoscope system controlling apparatus 30, the DC power source generating part 56 converts the power signal to direct-current power to supply power to each part of the operating unit 2. More specifically, the DC power source generating part 56 generates power to be utilized within the operating unit 2 based on the received power signal, and supplies power to each part of the operating unit 2.

The status signal demodulating part 57 that comprises the transmission and reception circuit 11a demodulates received status signals and sends the status signals after demodulation to the status management part 52. The image pickup signal demodulating part 58 comprising the transmission and reception circuit 11a demodulates received image pickup signals and sends the image pickup signals after demodulation to the image memory 53.

The control signal modulating part 59 comprising the transmission and reception circuit 11b modulates a control signal sent from the status management part 52 by, for example, frequency modulation, and sends the control signal after modulation to the signal synthesizing part 60. Further, the signal synthesizing part 60 comprising the transmission and reception circuit 11b synthesizes a power signal that was sent to the operating unit 2 from the endoscope system controlling apparatus 30 and the control signal after modulation, and sends the signal after synthesis to the inserting unit 3.

The status signal modulating part 61 comprising the transmission and reception circuit 19b modulates a status signal that was sent from a status signal synthesizing part 67 by, for example, frequency modulation, and sends the status signal after modulation to the status signal demodulating part 57. The image pickup signal modulating part 62 comprising the transmission and reception circuit 19b modulates an image pickup signal that was sent from the image pickup unit 70, and sends the image pickup signal after modulation to the image pickup signal demodulating part 58.

The control signal demodulating part 63 that comprises the transmission and reception circuit 19a demodulates control signals that are sent from the signal separating part 65, and sends the control signals after demodulation to an identification information memory 66 and an image pickup unit 70. The signal separating part 65 comprising the transmission and reception circuit 19a separates a signal that was sent from the signal synthesizing part 60 into a power signal and a control signal, and sends the control signal to the control signal demodulating part 63 and the power signal to the DC power source generating part 64.

After receiving the power signal that was sent from the signal separating part 65, the DC power source generating part 64 as a power generating part converts the power signal into direct-current power and supplies the power to each part of the inserting unit 3. More specifically, the DC power source generating part 64 generates power to be utilized inside the inserting unit 3 based on the received power signal and supplies the power to each part of the inserting unit 3. The identification information memory 66 is configured, for example, as a non-volatile rewritable recording part in which model information of the endoscope 1 and information specific to individual devices and the like is recorded. Further, the identification information memory 66 sends a signal that is based on information stored in the identification information memory 66 and on the status of a control signal sent from the control signal demodulating part 63 to the status signal synthesizing part 67. The status signal synthesizing part 67 synthesizes the signal that was sent from the identification information memory 66, a transparency signal and a contact pressure signal that were sent from the sensing unit 68, a present location signal sent from the motion controlling unit 69, and an amplification factor signal sent from the image pickup unit 70, and sends the thus-synthesized status signal to the status signal modulating part 61.

As shown in FIG. 6, the image pickup unit 70 as an image pickup part has an image pickup device 22, an ADC 70a as an analog/digital conversion circuit (hereunder abbreviated to "ADC"), an amplification factor control part 70b, and an image pickup device driving part 70c. After receiving a control signal that was sent from the control signal demodulating part 63, more specifically, an image pickup control signal, the image pickup device driving part 70c sends the image pickup control signal to the image pickup device 22, the ADC 70a and the amplification factor control part 70b. The image pickup device driving part 70c then drives each part to which it has sent the image pickup control signal based on the state of the image pickup control signal. Based on the contents of the control signal that was sent from the image pickup device driving part 70c, i.e. the amplification factor control signal, and the image pickup control signal, the amplification factor control part 70b sends a signal for performing sensitivity control, i.e. a sensitivity control signal, to the image pickup device 22, and sends an amplification factor signal that was obtained by converting an amplification factor based on the adjusted sensitivity to a digital signal to the status signal synthesizing part 67. The image pickup device 22 photographs the interior of the body of the examinee based on the state of the image pickup control signal and the sensitivity control signal. The images captured inside the body of the examinee are sent to the ADC 70a. Upon receiving the images of the interior of the examinee's body, the ADC 70a converts the images of the interior of the examinee's body to digital signals and sends the digital signals, i.e. image pickup signals, to the image pickup signal modulating part 62.

As shown in FIG. 7, in order to detect the state of contact of the tip part of the inserting unit 3 with respect to the interior of the examinee's body, the sensing unit 68 has the contact sensors 68a (see FIG. 1) that are provided at the tip part of the inserting unit 3, an ADC 68b, the transparency sensor 68c (see FIG. 1) that is provided in the vicinity of a transparent tube portion among the various conduits 3a in order to detect a contamination state inside the various conduits 3a, and an ADC 68d. The contact sensors 68a acquire the contact pressure when the tip part of the inserting unit 3 contacts against the examinee's body, and send the acquired contact pressure value to the ADC 68b. The ADC 68b converts the contact pressure value to a digital signal, and sends a contact pressure signal that is the signal after conversion to the status signal synthesizing part 67. The transparency sensor 68c receives reflected light that is generated by the illumination light being reflected within the examinee's body. The transparency sensor 68c determines a transparency value based on the strength of the reflected light that was received, and sends the transparency value to the ADC 68d. The ADC 68d converts the transparency value to a digital signal, and sends the transparency signal that is the post-conversion signal to the status signal synthesizing part 67.

As shown in FIG. 8, the motion controlling unit 69 has an encoder 69a, an actuator 69b used when performing a bending operation for the inserting unit 3, and an actuator driving part 69c that is provided for driving the actuator 69b. The actuator driving part 69c drives the actuator 69b as far as a control target position based on the state of a control signal, i.e. a target position signal, that was sent from the control signal demodulating part 63. The encoder 69a sends the driving status of the actuator 69b, i.e. a signal indicating the present position of the actuator 69b, to the status signal synthesizing part 67 via the actuator driving part 69c.

As a first modification example according to this embodiment, as shown in FIG. 9, a surgical flexible endoscope 3A can be connected to the operating unit 2 of the endoscope 1. The surgical flexible endoscope 3A is configured with a smaller outer diameter than the inserting unit 3, and has various conduits 3c that include fewer conduits than the various conduits 3a of the inserting unit 3. Other than the aforementioned parts, the surgical flexible endoscope 3A and the inserting unit 3 have the same configuration. More specifically, the surgical flexible endoscope 3A has a structure that can send and receive power signals, control signals and the like to and from the operating unit 2 in a non-contact manner, and has a dimensional shape that can be detachably connected to the connector portion 2a of the operating unit 2. Further, a tube unit 5A having various conduits 5b that correspond to the number of conduits of the various conduits 3c can be detachably connected to the surgical flexible endoscope 3A. A tube connector 7A is provided at the tip part of the tube unit 5A, and has a configuration that is attachable/detachable with respect to the endoscope system controlling apparatus 30.

Further, as a second modification example according to the present embodiment, as shown in FIG. 10, a conventional endoscope 1A can be connected to an endoscope system controlling apparatus 30A through an adapter 80. The endoscope system controlling apparatus 30A has a connector 49 on its outer surface, and is internally provided with a signal wire 80a, described later, and a signal wire that can connect to the image pickup signal processing unit 39. Other that the above described parts, the endoscope system controlling apparatus 30A and the endoscope system controlling apparatus 30 have the same configuration.

As shown in FIG. 11, the adapter 80 has a signal wire 80a, a light guiding passage 80b, air/water supply conduits 80c, and peripheral grooves 80d. The signal wire 80a is configured such that it can be connected with the image pickup signal processing unit 39 inside the endoscope system controlling apparatus 30A, and when the endoscope 1A is connected to the adapter 80, it is possible to send image pickup signals of the interior of the examinee's body that were photographed by the endoscope 1A. The light guiding passage 80b is a light guide such as optical fiber, and by connecting the light guiding passage 80b with an unshown light guide part, such as an optical fiber light guide, of the endoscope 1A, an illumination light that is supplied from the endoscope system controlling apparatus 30A can be guided to the endoscope 1A. The air/water supply conduits 80c are conduits that allow unshown various conduits of the endoscope 1A and conduits that are internally comprised by the endoscope system controlling apparatus 30A to communicate when the endoscope 1A is connected to the adapter 80. The peripheral grooves 80d and the ball plungers 31c are configured such that they can engage with each other, and by this configuration the endoscope system controlling apparatus 30 and the adapter 80 are attachable/detachable with respect to each other.

A video system center 81 is connected to the conventional endoscope 1A via a cable 81a. The video system center 81 has a connector 81b, and is connected to a connector 49 of the endoscope system controlling apparatus 30A through a cable 81c that is connected to the connector 81b. The connector 49 is connected to the system control unit 38 inside the endoscope system controlling apparatus 30A.

According to the endoscope 1 of this embodiment, as long as a portion that is connected to the operating unit 2 has a configuration that can send and receive power signals and control signals and the like in a non-contact manner, and has a dimensional shape that can be connected to the connector portion 2a of the operating unit 2, attachment and detachment of the inserting unit 3 to and from the operating unit 2 can be freely performed irrespective of the type of the inserting unit 3. As a result, using the common operating unit 2 it is possible to connect various types of inserting unit 3 that have the aforementioned configuration and aforementioned dimensional shape.

Since the endoscope 1 of this embodiment is configured to be able to send and receive various signals between the operating unit 2 and the inserting unit 3 in a non-contact manner, it is possible to decrease projections and depressions on the exterior thereof to thereby enhance detergency. Further, since the contact points of the endoscope 1 of this embodiment will not deteriorate due to corrosion or the like, the endoscope 1 can be used while maintaining the electrical properties thereof in a stable state.

Second Embodiment

FIGS. 12 to 17 are views that relate to a second embodiment of this invention. In this connection, a detailed description of parts that have the same configuration as those of the first embodiment is omitted. In addition, the same symbols are used to denote components that are the same as those in the first embodiment, and a description of these components is omitted.

Figure 12:
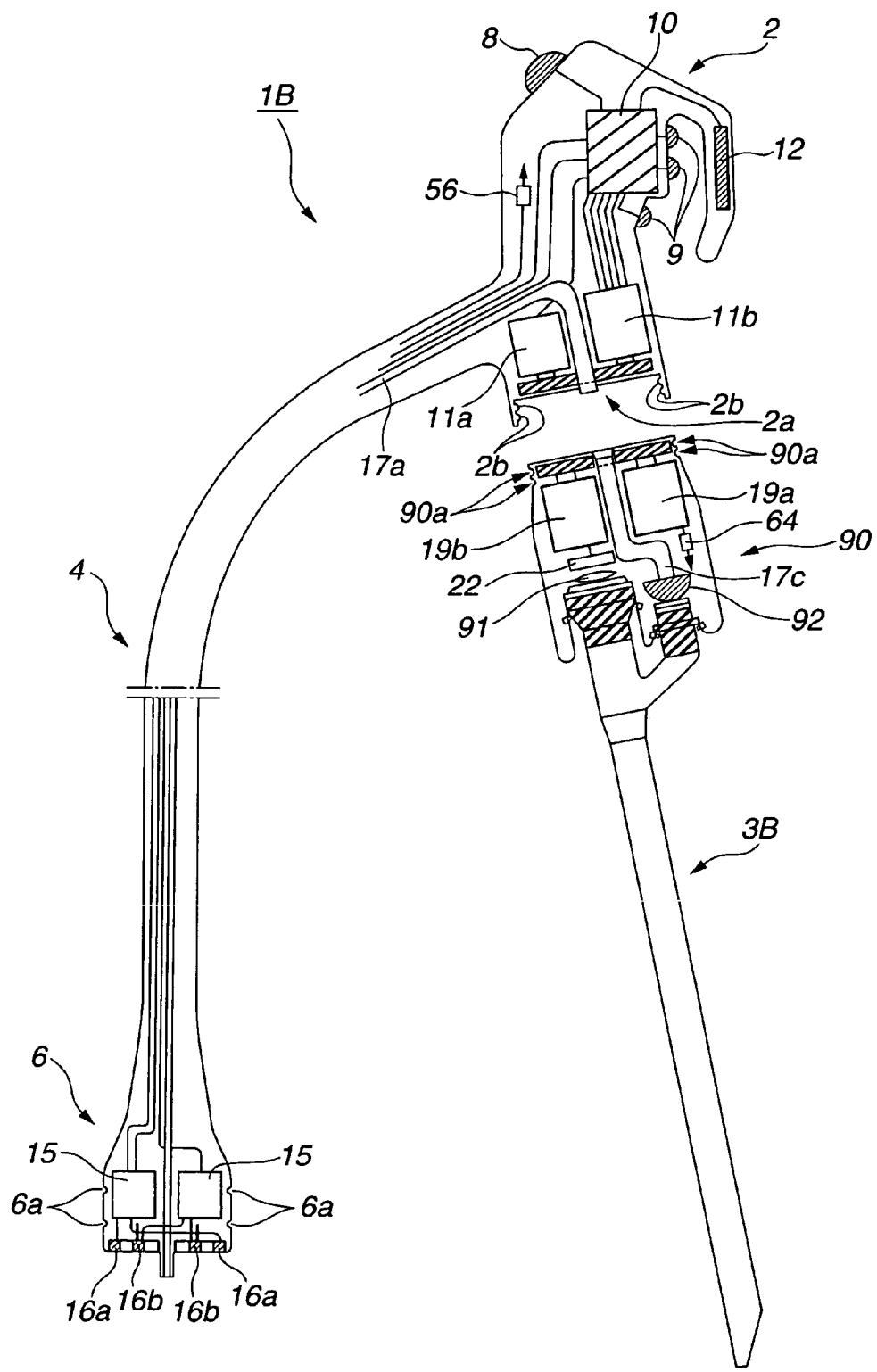
FIG. 12 is a view for describing the configuration of an endoscope according to a second embodiment.
Figure 13:
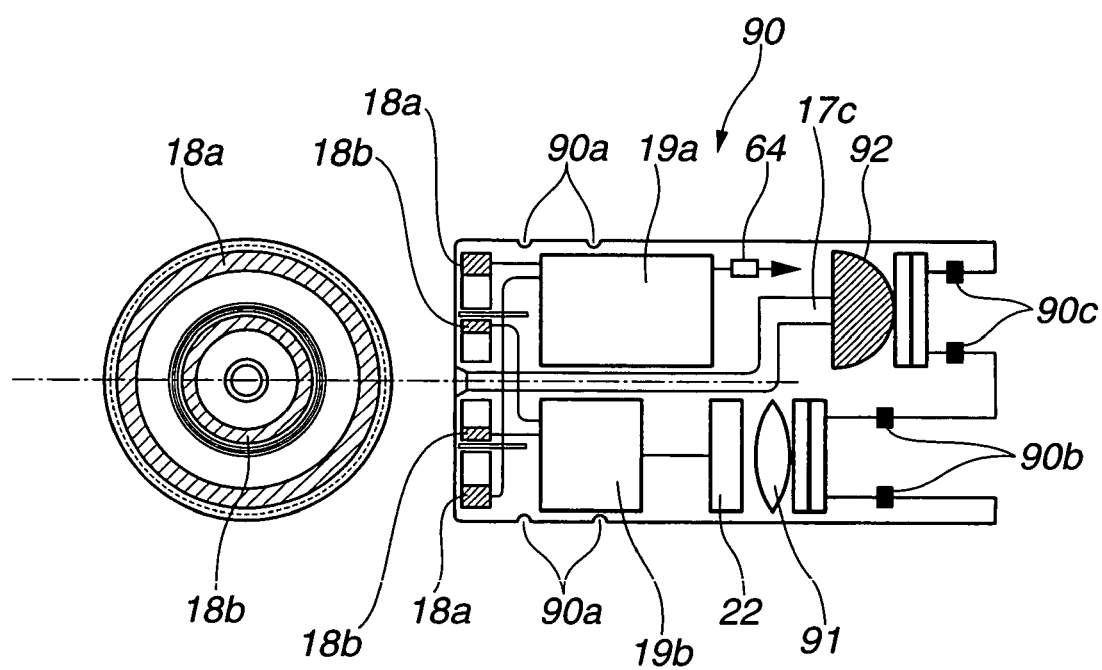
FIG. 13 is a view for describing the configuration of a camera head adapter of an endoscope according to the second embodiment.
Figure 14:
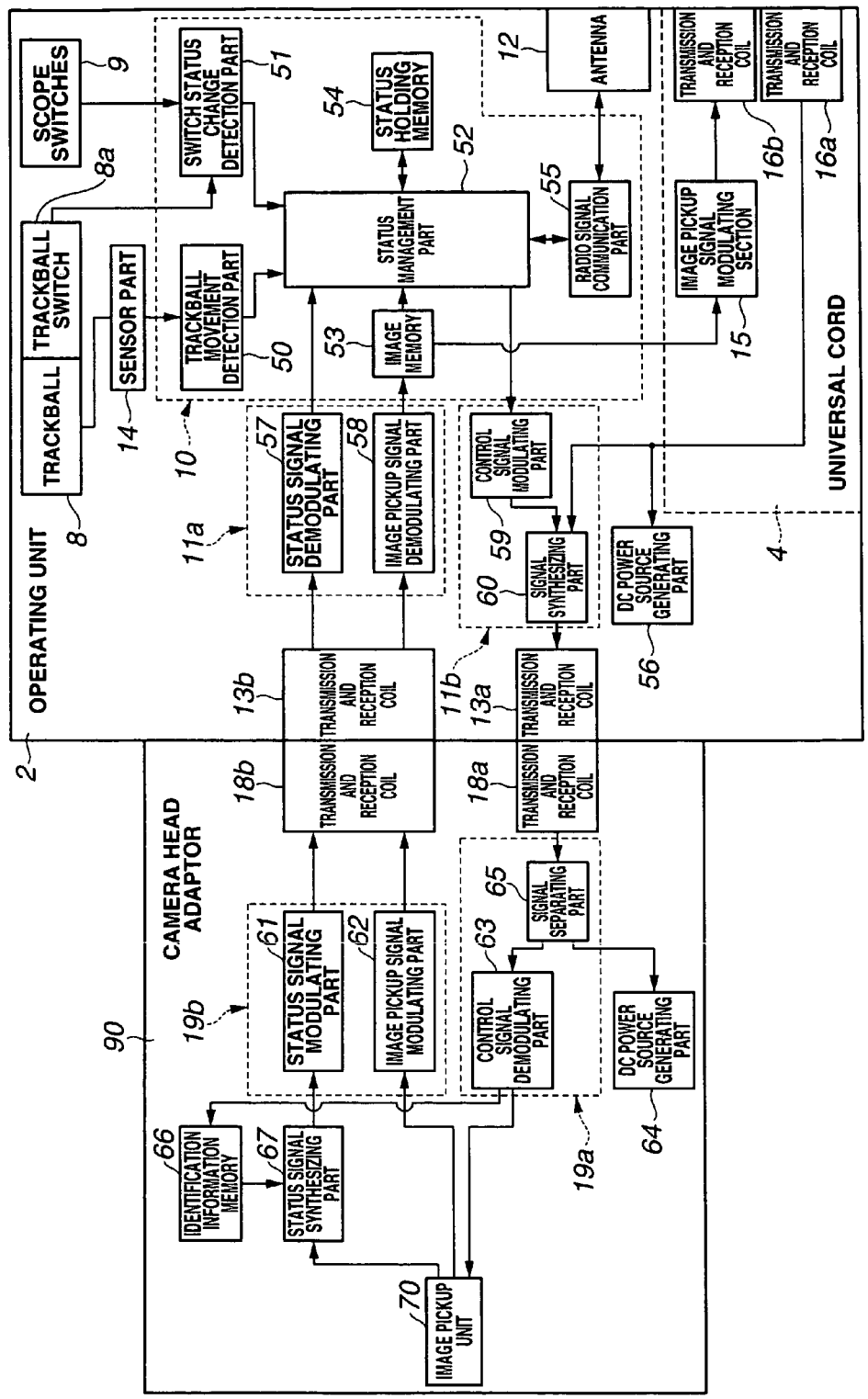
FIG. 14 is a block diagram showing the internal configuration of an operating unit and a camera head adapter of the endoscope according to the second embodiment.
Figure 15:
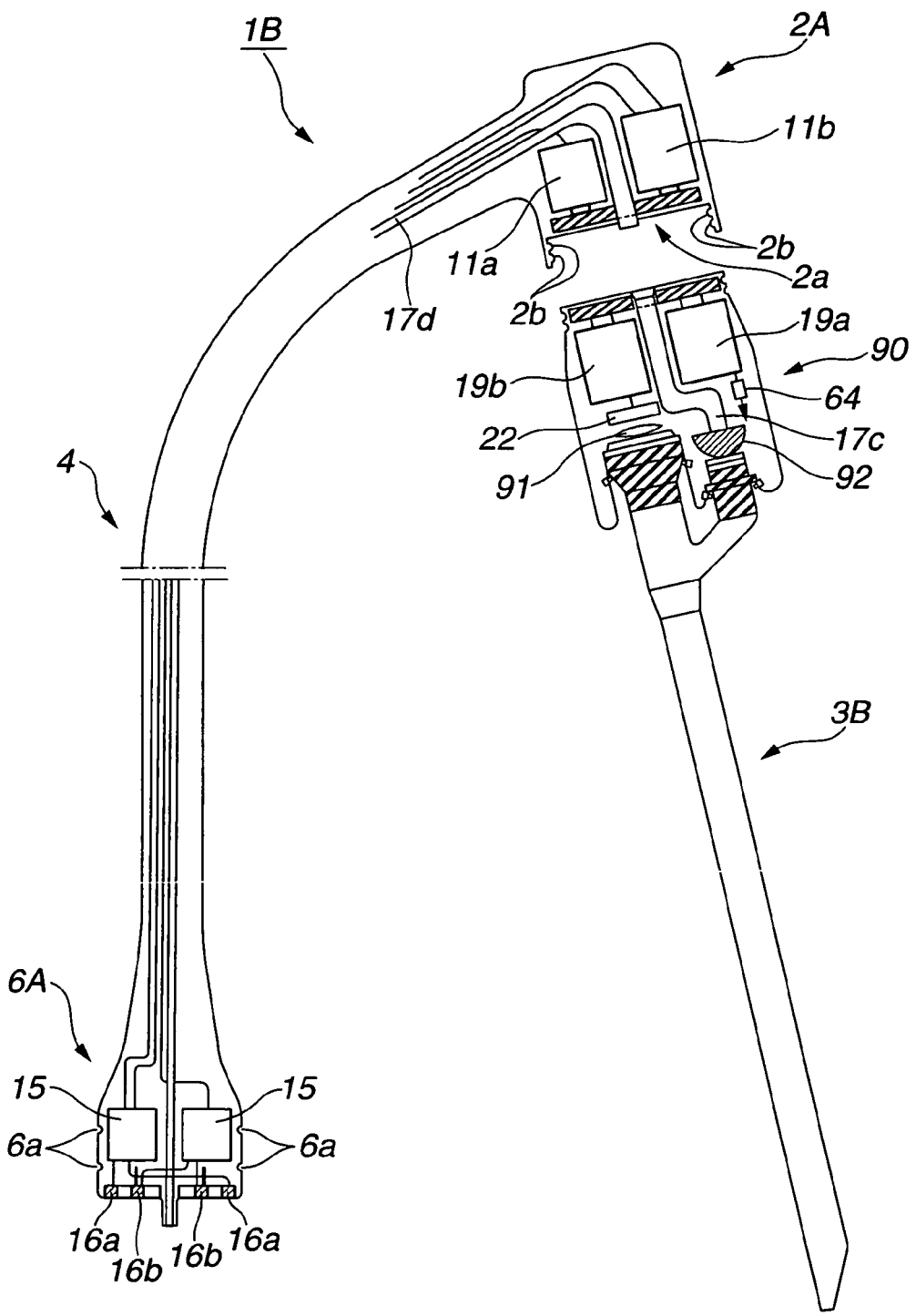
FIG. 15 is a sectional view illustrating a modification example of the endoscope according to the second embodiment.
Figure 16:
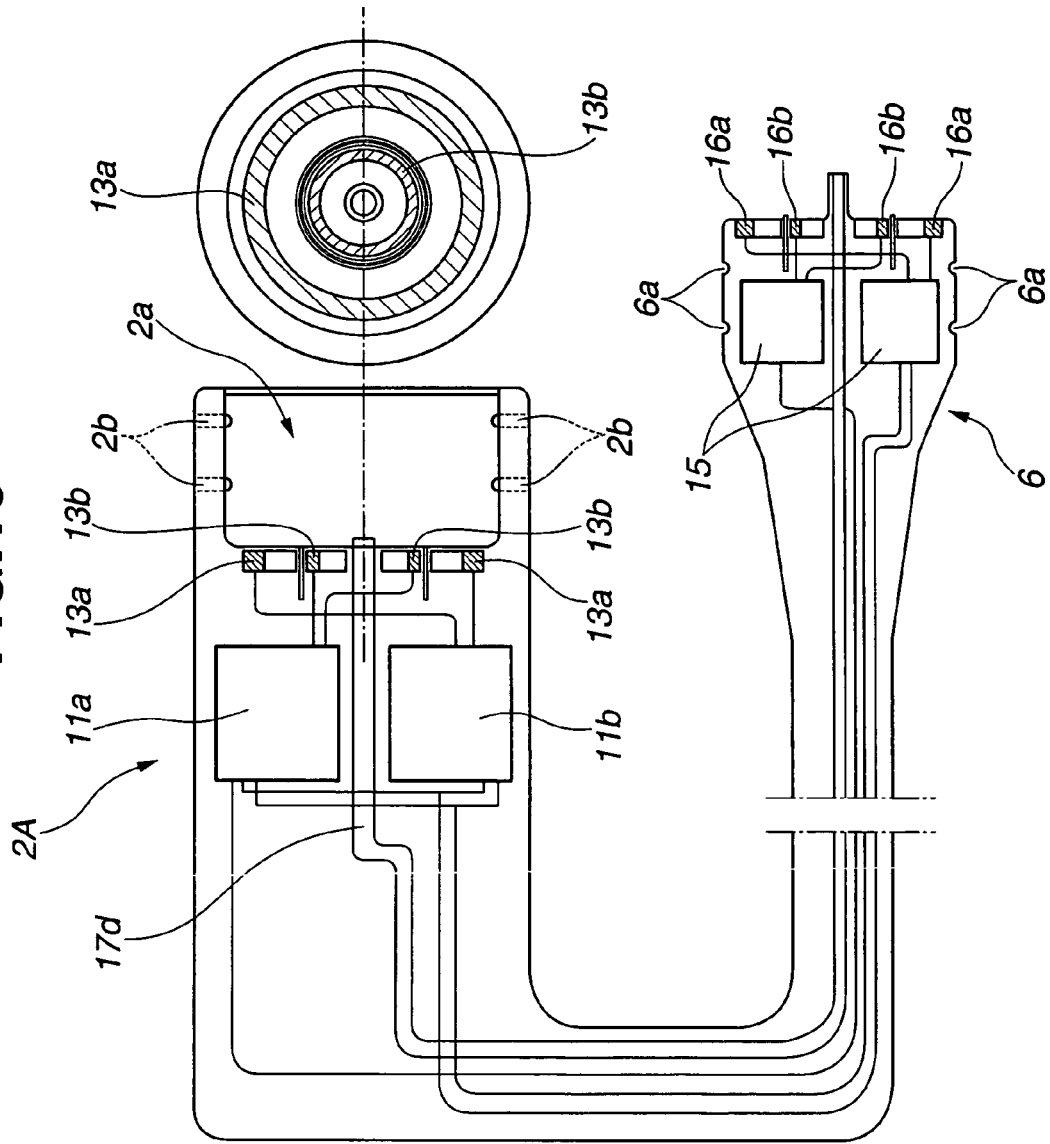
FIG. 16 is a sectional view of a cable unit of the modification example of the endoscope according to the second embodiment.
Figure 17:
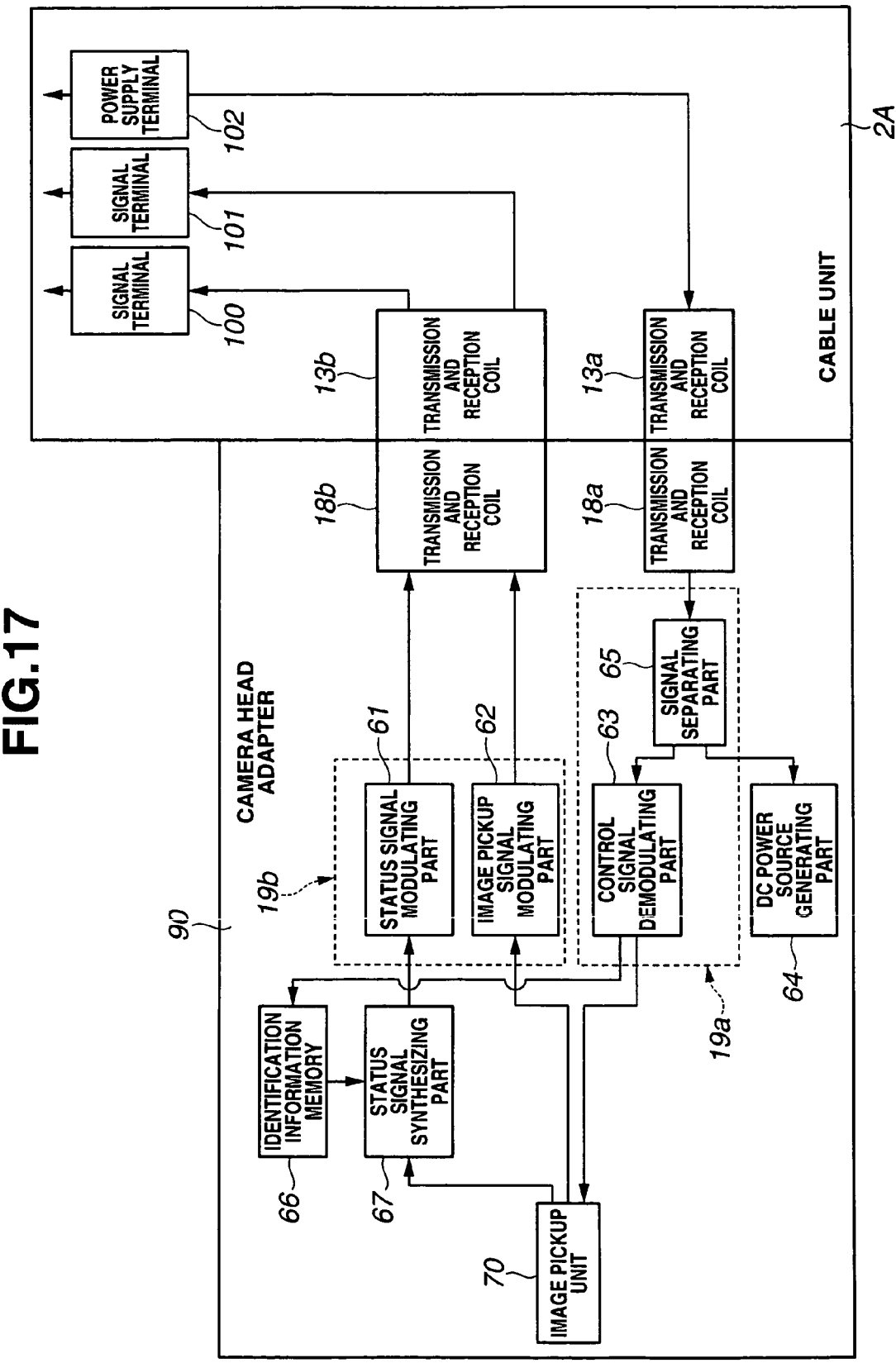
FIG. 17 is a block diagram showing the internal configuration of the cable unit and a camera head adapter of the modification example of the endoscope according to the second embodiment.

FIG. 12 is a view for describing the configuration of an endoscope according to this embodiment. FIG. 13 is a view for describing the configuration of a camera head adapter of the endoscope according to this embodiment. FIG. 14 is a block diagram showing the internal configuration of an operating unit and a camera head adapter of the endoscope according to this embodiment. FIG. 15 is a sectional view illustrating a modification example of the endoscope according to this embodiment. FIG. 16 is a sectional view of a cable unit of the modification example of the endoscope according to this embodiment. FIG. 17 is a block diagram showing the internal configuration of the cable unit and a camera head adapter of the modification example of the endoscope according to this embodiment.

As shown in FIG. 12, an endoscope 1B of this embodiment comprises an operating unit 2, a camera head adapter 90 as a connection adapter, and a rigid endoscope 3B as an inserting unit. The operating unit 2 is configured in the same manner as in the first embodiment and has the same components. As shown in FIG. 13, peripheral grooves 90a that are concave portions are provided on the outer peripheral surface of the camera head adapter 90 as a connection adapter side engaging portion. The ball plungers 2b have a structure that can engage with the peripheral grooves 90a, and by this configuration the camera head adapter 90 has a structure that is attachable/detachable and rotatable with respect to the operating unit 2. The camera head adapter 90 also has fixing members 90b and 90c that comprise annular elastic members or the like. The rigid endoscope 3B is configured in a conduit shape that has a bifurcated rear anchor part. The two rear anchor parts are configured to be capable of engaging with the fixing members 90b and 90c, respectively. According to this configuration, the rigid endoscope 3B has a structure that is attachable/detachable with respect to the camera head adapter 90. In this embodiment, when the ball plungers 2b and the peripheral grooves 90a are engaged, the transmission and reception coils 13a and 13b that are provided in the operating unit 2 and the transmission and reception coils 18a and 18b that are provided in the camera head adapter 90 are disposed at positions that are physically separated.

As shown in FIG. 13, the camera head adapter 90 internally comprises a light guide fiber 17c, transmission and reception coils 18a and 18b, transmission and reception circuits 19a and 19b, an image pickup device 22, a lens 91 and a lens 92.

The lens 91 is provided at a position whereby an image of the interior of the examinee's body can be formed on the image pickup device 22. The lens 92 is provided at one end of the light guide fiber 17c, at a position that condenses light that passed through the light guide fiber 17c at an end part of an unshown light guide fiber at a rear anchor part of the rigid endoscope 3B.

Similarly to the first embodiment, since the sectional form of the transmission and reception coils 18a and 18b is annular, when the camera head adapter 90 is connected to the operating unit 2, sending and receiving of various signals can be performed in a non-contact manner by electromagnetic induction with the transmission and reception coils 13a and 13b that have a similar structure. In this connection, the power required to drive each part provided in the operating unit 2 and the camera head adapter 90 is supplied to the operating unit 2 and the camera head adapter 90a as a power signal that was encoded at the endoscope system controlling apparatus 30. More specifically, a power signal that was sent from the endoscope system controlling apparatus 30 is sent in a non-contact manner to the transmission and reception coil 16a from the transmission and reception coil 31a, and thereafter is sent to the transmission and reception coil 13a as a power signal sending part via the transmission and reception circuit 11b. Upon receiving the power signal, the transmission and reception coil 13a sends the power signal in a non-contact manner by electromagnetic induction to the transmission and reception coil 18a. The transmission and reception coil 18a as a power signal receiving part receives the power signal in a non-contact manner by electromagnetic induction. Based on the received power signal, the DC power source generating part 56 generates power to be utilized inside the operating unit 2 and supplies the power to each part of the operating unit 2.

As shown in FIG. 12, a light guide fiber 17a having the same configuration as the first light guide part is provided as a third light guide part within the operating unit 2 and the universal cord 4. Further, as shown in FIG. 13, a light guide fiber 17c is provided as a fourth light guide part inside the camera head adapter 90. The light guide fiber 17a and the light guide fiber 17c are configured such that they communicate when the camera head adapter 90 is connected to the operating unit 2, and through this configuration, an illumination light that was supplied from the endoscope system controlling apparatus 30 is irradiated inside the body of the examinee from the tip part of the rigid endoscope 3B.

The internal configuration of the camera head adapter 90 is as illustrated in FIG. 14. Unlike the inserting unit 3 of the endoscope 1 of the first embodiment, the rigid endoscope 3B does not have the angle member 21, the contact sensors 68a or the transparency sensor 68c. For this reason, unlike the inserting unit 3 of endoscope 1 of the first embodiment, the camera head adapter 90 does not have the sensing unit 68 or the motion controlling unit 69. Other than the aforementioned parts, the camera head adapter 90 has substantially the same function as the inserting unit 3. More specifically, the camera head adapter 90 has a function that can send and receive power signals, control signals and the like in a non-contact manner to and from the operating unit 2.

As a modification example according to this embodiment, as shown in FIG. 15, a cable unit 2A having the universal cord 4 configured therewith in an integrated manner can also be connected to the camera head adapter 90 of the endoscope 1B.

The cable unit 2A internally comprises a light guide fiber 17d as a third light guide part. At the tip part of the cable unit 2A is provided a scope connector 6A that has the same configuration as the scope connector 6.

As shown in FIG. 15, the light guide fiber 17d having the same configuration as the first light guide part is provided as a third light guide part within the cable unit 2A, and as shown in FIG. 15, a light guide fiber 17c is provided as a fourth light guide part within the camera head adapter 90. The light guide fiber 17d and the light guide fiber 17c are configured such that they communicate when the camera head adapter 90 is connected to the cable unit 2A, and through this configuration an illumination light supplied from the endoscope system controlling apparatus 30 is irradiated inside the body of the examinee from the tip part of the rigid endoscope 3B through the lens 92 of the camera head adapter 90.

The cable unit 2A has an internal configuration as shown in FIG. 16. Unlike the operating unit 2 of the endoscope 1B shown in FIG. 12, the cable unit 2A does not have the trackball 8, the scope switches 9 or the antenna 12. Therefore, the cable unit 2A does not have the control circuit 10 and sensors 14a and 14b that are required in order to detect a movement of, or the existence/non-existence of a pressing force on, the trackball 8 and the existence/non-existence of a pressing force on the scope switches 9. Furthermore, since the cable unit 2A does not have the control circuit 10, the transmission and reception circuits 11a and 11b are directly connected to the image pickup signal modulating part 15. Apart from the above described parts, the cable unit 2A has the same structure and the like as the operating unit 2. More specifically, the cable unit 2A has a configuration that can send and receive power signals, control signals and the like to and from the camera head adapter 90 in a non-contact manner, and has a dimensional shape that can be detachably connected to the camera head adapter 90.

Further, as shown in FIG. 17, inside the cable unit 2A the transmission and reception coil 13a is connected to a power supply terminal 102, and the transmission and reception coil 13b is connected to signal terminals 100 and 101. The signal terminals 100 and 101 and the power supply terminal 102 are connected to the transmission and reception circuits 11a and 11b, respectively.

According to the endoscope 1B of this embodiment, as long as a portion that is connected to camera head adapter 90 has a configuration that can send and receive power signals and control signals and the like in a non-contact manner, and has a dimensional shape that can be connected to the camera unit 90, attachment and detachment of the operating unit 2 to and from the camera unit 90 can be performed irrespective of the type and the like of the operating unit 2. Further, as long as the rigid endoscope 3B has a dimensional shape that can be connected to the camera unit 90, attachment and detachment of the rigid endoscope 3B to and from the camera unit 90 can be performed irrespective of the type and the like of the rigid endoscope 3B. As a result, using a common camera unit 90 it is possible to connect various types of the operating unit 2 and the rigid endoscope 3B that have the aforementioned configuration and aforementioned dimensional shape, and to share a flexible endoscope system.

Figure 18:
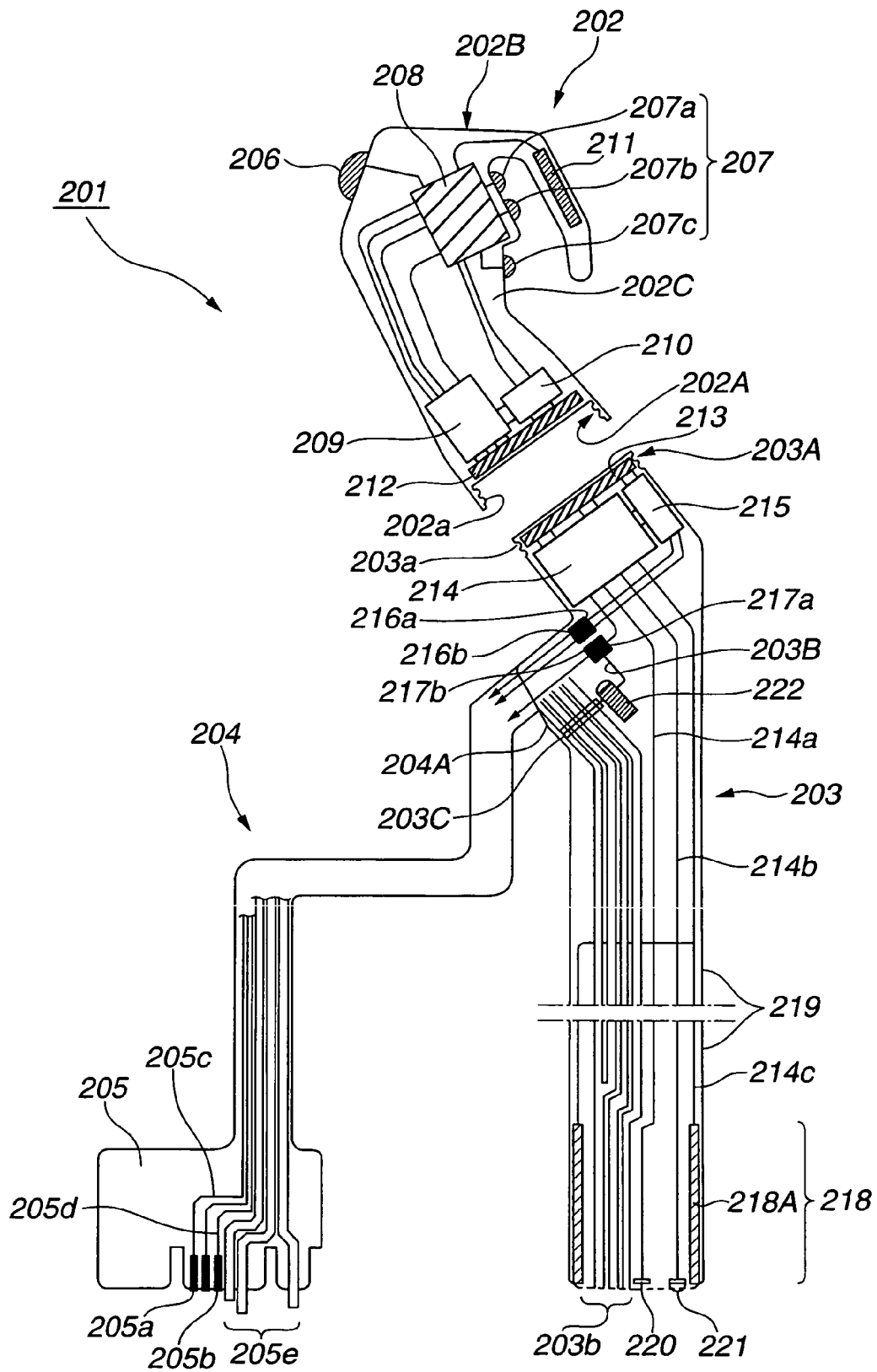
FIG. 18 is a schematic diagram showing the configuration of an endoscope according to a third embodiment.
Figure 19:
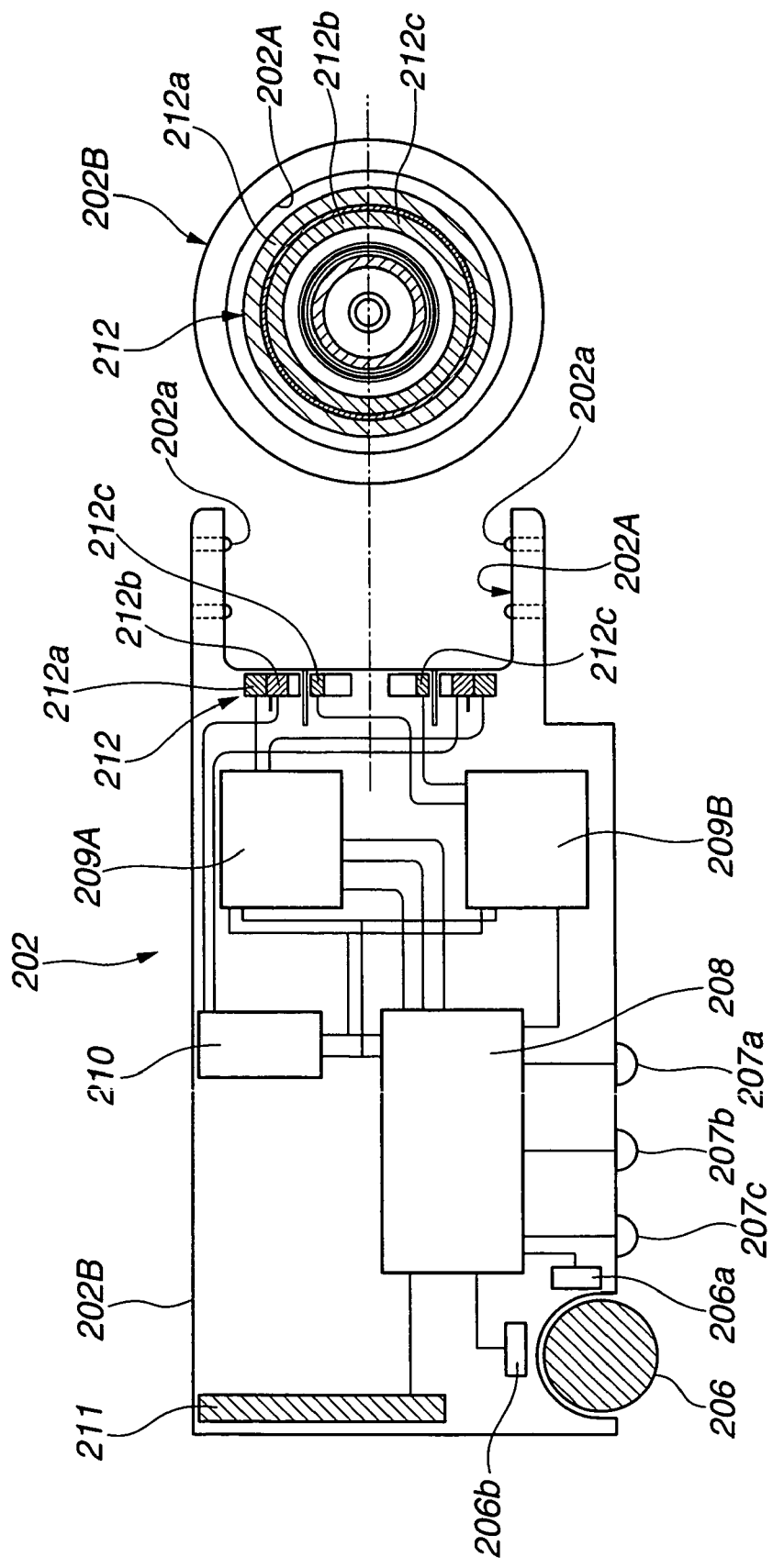
FIG. 19 is a view for describing the configuration of the operating unit shown in FIG. 18.
Figure 20:
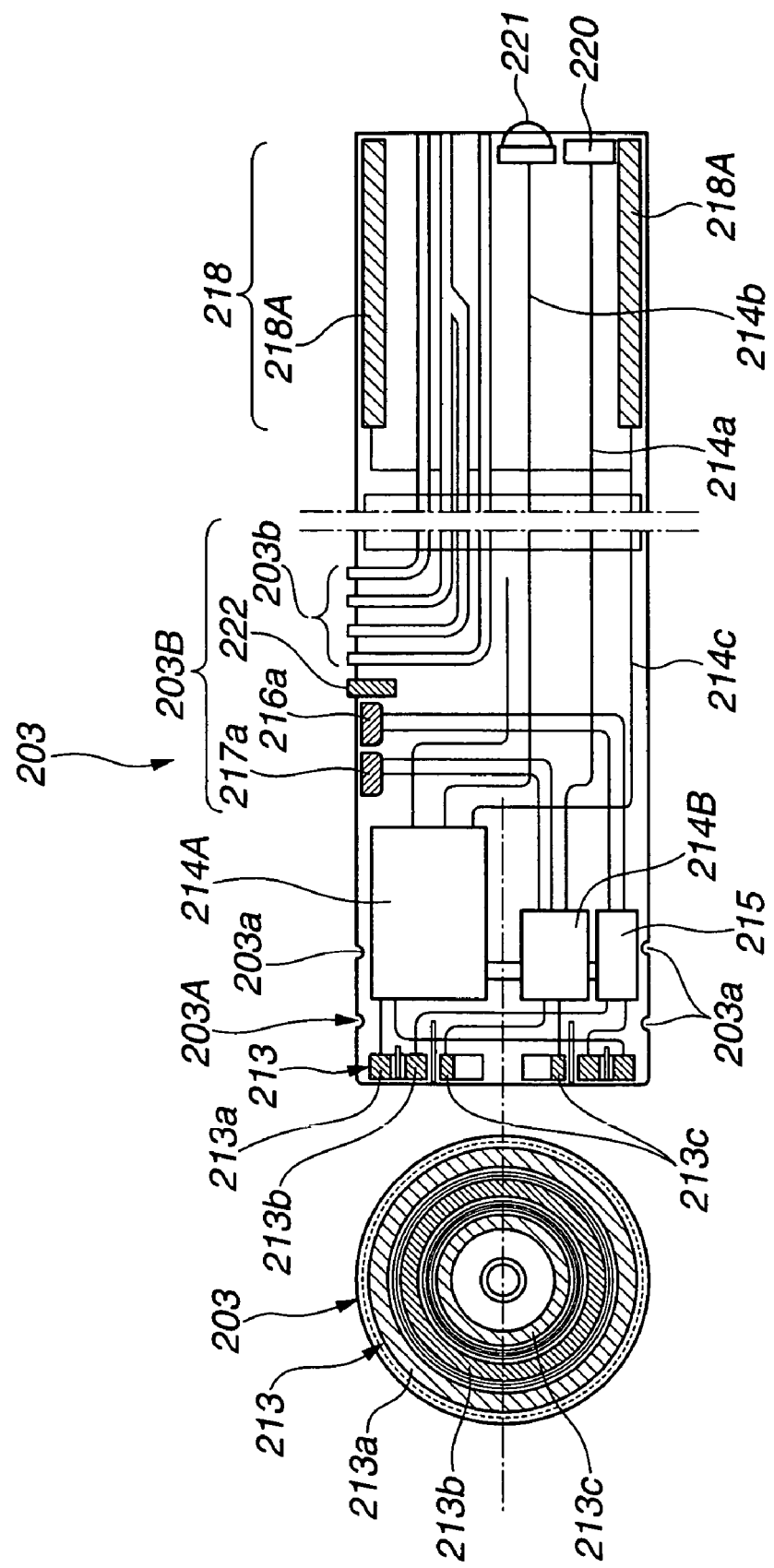
FIG. 20 is a view for describing the configuration of the inserting unit shown in FIG. 18.
Figure 21:
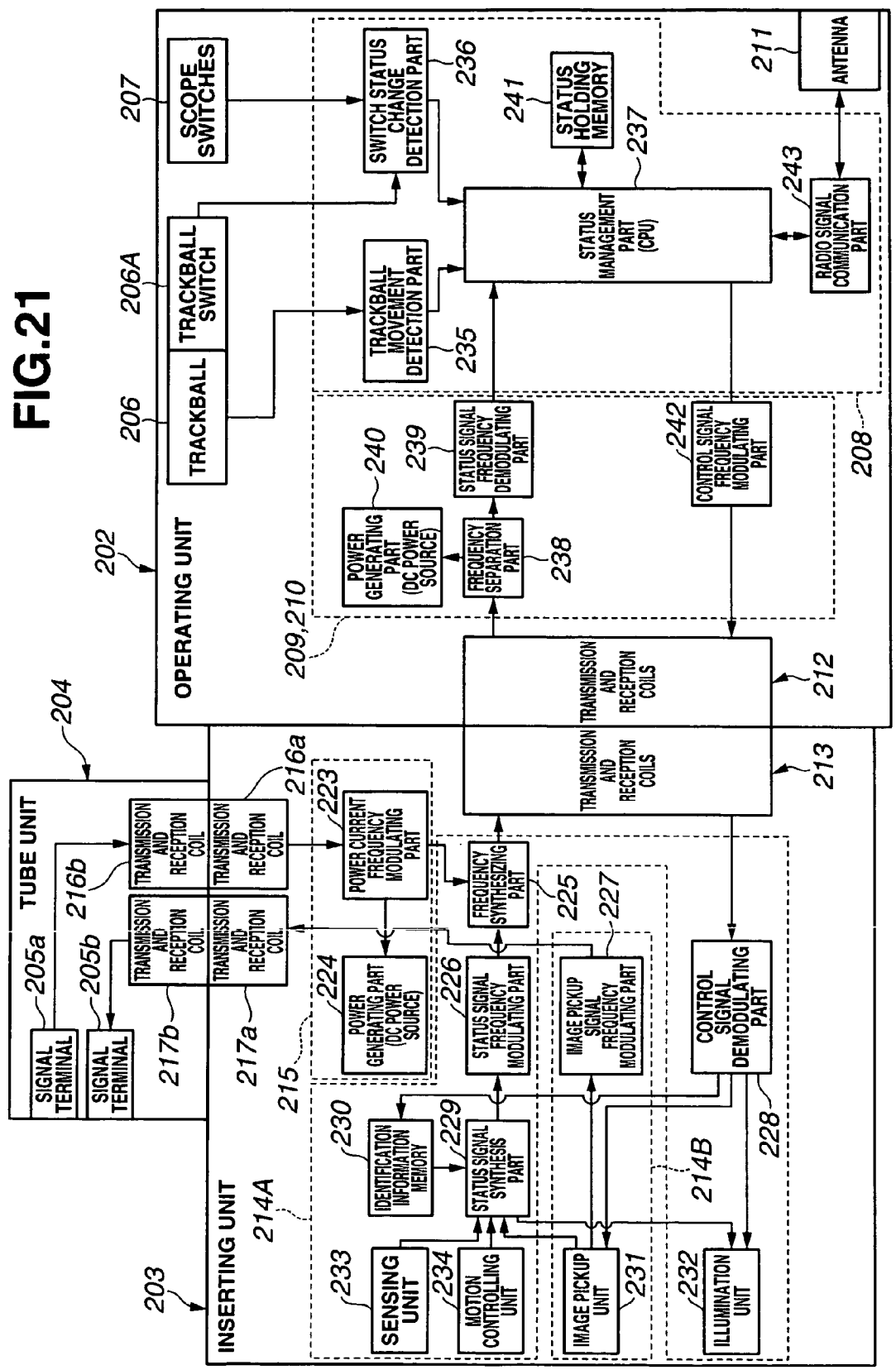
FIG. 21 is a block diagram showing the overall electrical configuration of the endoscope shown in FIG. 18.
Figure 22:
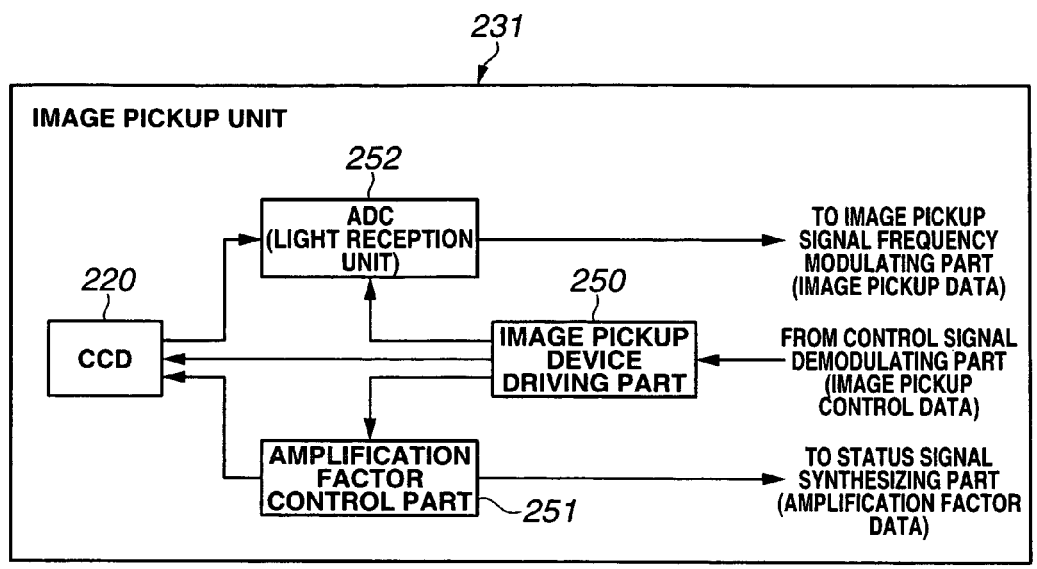
FIG. 22 is a block diagram showing the internal configuration of an image pickup unit provided in the inserting unit shown in FIG. 21.
Figure 23:
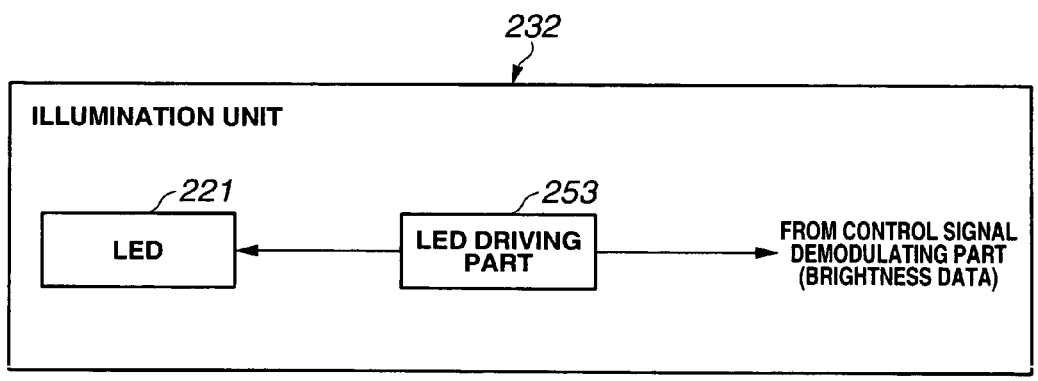
FIG. 23 is a block diagram showing the internal configuration of an illumination unit provided in the inserting unit shown in FIG. 21.
Figure 24:
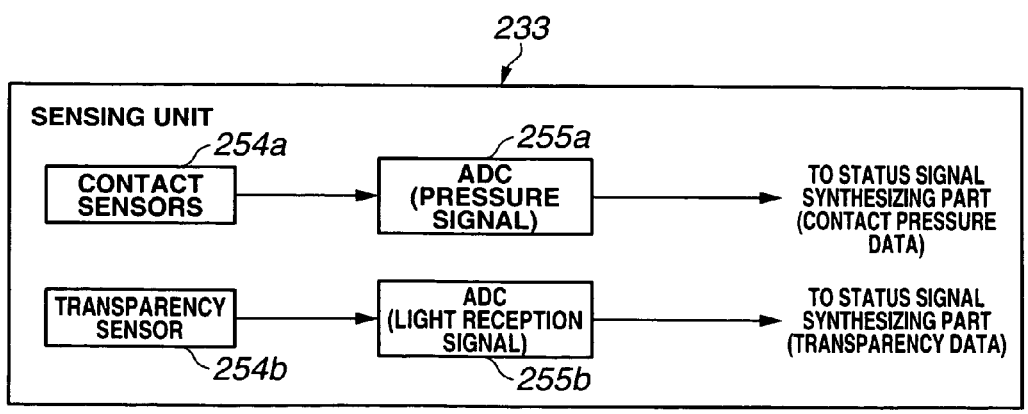
FIG. 24 is a block diagram showing the internal configuration of a sensing unit provided in the inserting unit shown in FIG. 21.
Figure 25:
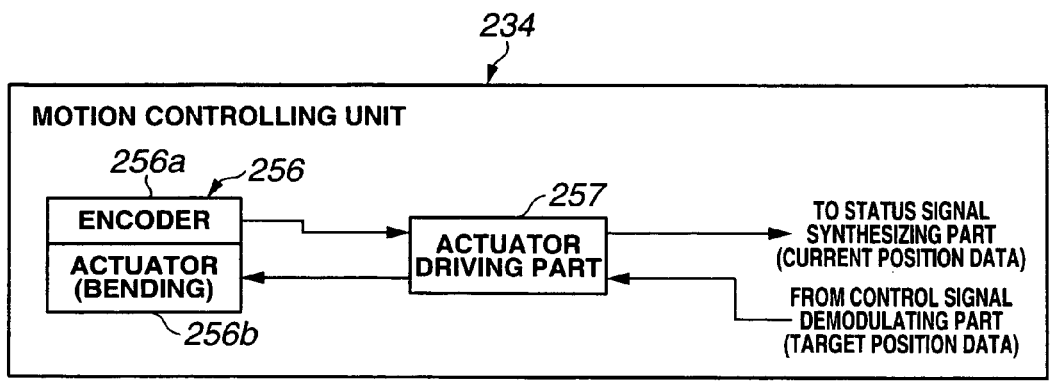
FIG. 25 is a block diagram showing the internal configuration of a motion controlling unit provided in the inserting unit shown in FIG. 21.
Figure 26:
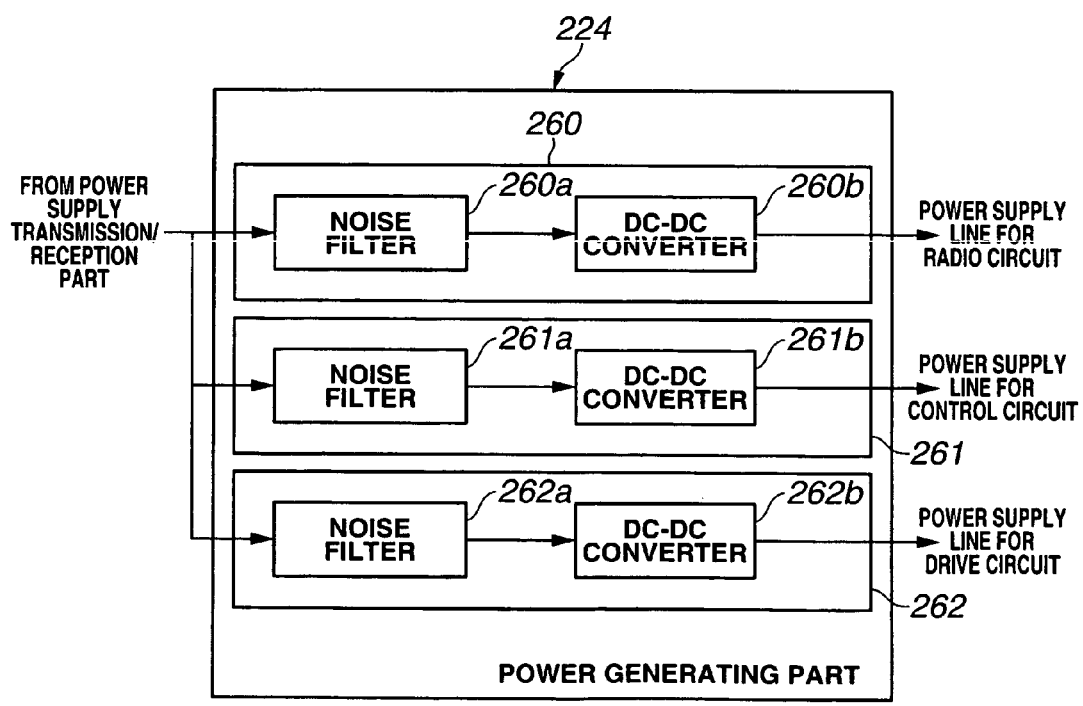
FIG. 26 is a block diagram showing the internal configuration of a power generating part provided in the inserting unit shown in FIG. 21.
Figure 27:
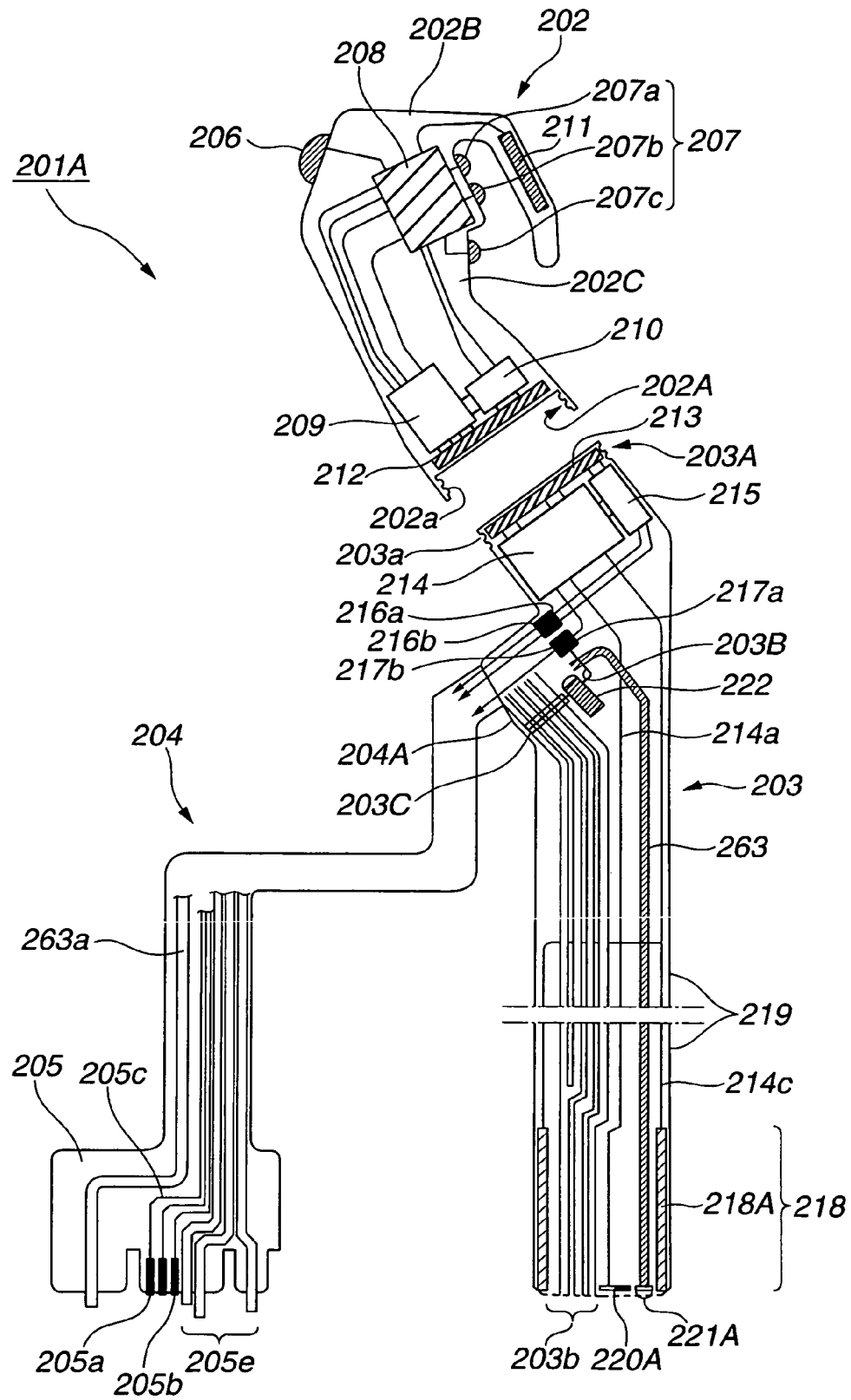
FIG. 27 is a configuration diagram for describing a first modification example of the endoscope according to the third embodiment.

FIGS. 18 to 27 relate to the third embodiment of this invention. FIG. 18 is a schematic diagram showing the configuration of an endoscope according to the third embodiment. FIG. 19 is a view for describing the configuration of the operating unit shown in FIG. 18. FIG. 20 is a view for describing the configuration of the inserting unit shown in FIG. 18. FIG. 21 is a block diagram showing the electrical configuration of the entire endoscope shown in FIG. 18. FIG. 22 is a block diagram showing the internal configuration of an image pickup unit provided in the inserting unit shown in FIG. 21. FIG. 23 is a block diagram showing the internal configuration of an illumination unit provided in the inserting unit shown in FIG. 21. FIG. 24 is a block diagram showing the internal configuration of a sensing unit provided in the inserting unit shown in FIG. 21. FIG. 25 is a block diagram showing the internal configuration of a motion controlling unit provided in the inserting unit shown in FIG. 21. FIG. 26 is a block diagram showing the internal configuration of a power generating section provided in the inserting unit shown in FIG. 21. FIG. 27 is a configuration diagram for describing a first modification example of the endoscope according to the third embodiment. Hereunder, a description of parts having the same configuration as those of the first embodiment and second embodiment is omitted. Further, the same symbols are used to denote components that are the same as those in the first embodiment and second embodiment, and a description of these components is omitted.

As shown in FIG. 18, an endoscope 201 according to this embodiment comprises an operating unit 202, an inserting unit 203 and a tube unit 204. The operating unit 202 has a connector portion 202A at the bottom thereof, and as shown in FIG. 19, ball plungers 202a are provided on the inner peripheral surface of the connector portion 202A.

As shown in FIG. 20, peripheral grooves 203a are provided on the outer peripheral surface of the inserting unit 203. The ball plungers 202a and the peripheral grooves 203a are configured such that they can engage with each other. Accordingly, through this configuration the operating unit 202 and the inserting unit 203 are attachable/detachable and rotatable with respect to each other.

A connector portion 204A of the tube unit 204 is detachably connected to a connector portion 203B of the inserting unit 203. Within the tube unit 204 are provided a power supply wire 205c for supplying driving power to the inserting unit 203 and the operating unit 202, a signal wire 205d that carries out transmission of signals such as an image pickup device control signal and a drive system control signal, and various conduits 205e such as air supply and water supply conduits.

A scope connector 205 is provided at the tip part of the tube unit 204. In the scope connector 205 are provided a power supply terminal 205a that is electrically connected to the power supply wire 205c, and a signal terminal 205b that is electrically connected to the signal wire 205d.

At least one part of the scope connector 205 is, for example, connected to an unshown light source device that has a configuration similar to the endoscope system controlling apparatus 30 shown in FIG. 4. The unshown light source device as a power source supplies a power signal based on the electric power to be used to drive each part of the endoscope 201 through the power supply terminal 205a and the signal wire 205c of the connected scope connector 205. Further, the unshown light source device as a power source is configured to send and receive signals such as an image pickup device control signal and a drive system control signal via the signal terminal 205b.

The operating unit 202 has a main body part 202B. At one portion of the main body part 202B is provided a grip part 202C comprising a hook formed in a protruding manner. A trackball 206 and scope switches 207 are provided on the outer surface adjacent to the grip part 202C of the main body part 202B.

The trackball 206 is formed in the shape of a sphere, and a technician can perform various operations such as a settings change by rotating or pressing the trackball 206. The scope switches 207 comprise a first scope switch 207a, a second scope switch 207b and a third scope switch 207c. A technician can perform various operations such as supplying air or supplying water by pressing the scope switches 207a to 207c.

As shown in FIG. 18 and FIG. 19, the operating unit 202 internally comprises a control circuit 208 as a control part, transmission and reception/control circuits 209 (209A, 209B), a frequency modulation/power generating section 210, an antenna 211, transmission and reception coils 212 (212a-212c), and sensors 206a and 206b.

As shown in FIG. 18, the inserting unit 203 comprises, in order from the tip part side, a bending section 218 and a flexible tube section 219.

Further as shown in FIGS. 18 and 20, the inserting unit 203 internally comprises various conduits 203b that include a plurality of conduits, transmission and reception coils 213 (213a-213c), transmission and reception/control circuits 214 (214A, 214B) as drive control parts, various signal wires 214a-214c, a frequency modulation/power generating section 215, transmission and reception coils 216a and 217a, an angle member 218A, an image pickup device 220, an illumination element 221 and a leak detection mouth 222.

As the image pickup device 220, for example, a CMOS (Complementary Metal Oxide Semiconductor) or a CCD that is a charge image pickup device is used. Further, an LED or the like is used as the illumination element 221.

The various conduits 203b are configured to communicate through a connecting part 203C with various conduits 205e that are provided within the tube unit 204 when the tube unit 204 is connected to the inserting unit 203, and through this configuration, air supply and water supply and the like to the interior of the examinee's body can be performed.

In the operating unit 202, as shown in FIG. 19, the control circuit 208 receives the contents of an operation performed by a technician as signals from the scope switches 207 and the sensors 206a and 206b that are connected to the trackball 206, and sends control signals to each part based on the state of these signals. The control circuit 208 is connected to the antenna 211, and sends and receives control signals through the antenna 211 to and from an endoscope system controlling apparatus (not shown) that carries out various controls of the endoscope 201.

The control circuit 208 is also connected to the transmission and reception/control circuits 209 (209A, 209B). When the inserting unit 203 is connected to the operating unit 202, the control circuit 208 supplies control signals to the transmission and reception coils 212 through the transmission and reception/control circuits 209 (209A, 209B) to send the signals to the transmission and reception coils 213 provided in the inserting unit 203.

When the inserting unit 203 is connected to the operating unit 202, the control circuit 208 receives via the transmission and reception coils 212 and the transmission and reception/control circuits 209 (209A, 209B) a synthesized signal that includes a power signal, described later, a status signal, an image pickup signal (image signal) and a control signal, that is sent from the transmission and reception coils 213 provided in the inserting unit 203.

The control circuit 208 supplies the received synthesized signal to the frequency modulation/power generating section 210. The frequency modulation/power generating section 210 obtains the original power signal, status signal, image pickup signal and control signal from the synthesized signal by frequency separation processing, and supplies the power signal to a power generating part 240 that is described later. Further, the control circuit 208 supplies the status signal to a status signal demodulating part 239, described later, and the image pickup signal and control signal to a radio data communication part 243, described later. The radio data communication part 243 sends the image pickup signal and the control signal to an unshown endoscope system controlling apparatus through the antenna 211.

The transmission and reception coils 212 as a signal transmission and reception section include three transmission and reception coils 212a-212c as shown in FIG. 19. Since the sectional form of the transmission and reception coils 212 is annular, when the inserting unit 203 is connected to the operating unit 202, sending and receiving of various signals can be performed in a non-contact manner by electromagnetic induction with the transmission and reception coils 213 (213a-213c) that serve as a signal transmission and reception section and have a similar structure (see FIG. 20). The transmission frequencies of these various signals may be made different to each other to prevent or reduce interference.

According to this embodiment, among the three transmission and reception coils 212a-212c and the three transmission and reception coils 213a-213c, for example, signal transmission of control signals or the like is assigned to the transmission and reception coils 212a and 213a. Further, signal transmission of image pickup signals is assigned to the transmission and reception coils 212c and 213c for which there is little influence on signal transmission because they are near the rotational axis, and signal transmission of a synthesized signal including a power signal or a status signal is assigned to the transmission and reception coils 212b and 213b. Naturally, the assignment of signal transmission functions is not limited thereto, and the assigned functions may be changed and set as appropriate.

Further, since the sectional form of the transmission and reception coils 216b and 217b that are provided in the tube unit 204, described later, is also annular, similarly to the transmission and reception coils 212 provided in the operating unit 202, when the tube unit 204 is connected to the inserting unit 203, sending and receiving of various signals such as a power signal, described later, can be performed in a non-contact manner by electromagnetic induction with the transmission and reception coils 216a and 217a that are provided in the inserting unit 203.

According to this embodiment, the power required to drive each part provided in the operating unit 202 and the inserting unit 203 is supplied to the inserting unit 203 and the operating unit 202 by connection of the tube unit 204 to the inserting unit 203.

More specifically, power (a power signal) from an unshown light source device is supplied to the transmission and reception coil 216b through the power supply terminal 205a of the scope connector 205 and the power supply wire 205c of the tube unit 204. The transmission and reception coil 216b sends the power signal to the transmission and reception coil 216a of the inserting unit 203 in a non-contact manner by electromagnetic induction, and the transmission and reception coil 216a receives the power signal in a non-contact manner by electromagnetic induction.

In the inserting unit 203, the frequency modulation/power generating section 215 is connected to the transmission and reception coil 216a. When the tube unit 204 is connected to the inserting unit 203, the frequency modulation/power generating section 215 receives a power signal via the transmission and reception coil 216a and supplies the received power signal to a power generating part 224 that is described later. Further, the frequency modulation/power generating section 215 subjects the power signal to frequency modulation and supplies it to the transmission and reception/control circuit 214A.

The transmission and reception/control circuit 214A sends the frequency modulated power signal to the operating unit 202, and obtains a synthesized signal in which a status signal, an image pickup signal and a control signal are synthesized, and sends this synthesized signal to the transmission and reception coils 212 (212a-212c) of the operating unit 202 through the transmission and reception coils 213 (213a-213c). Further, when the operating unit 202 is connected to the inserting unit 203, the transmission and reception/control circuit 214A receives via the transmission and reception coils 213 (213a-213c) predetermined signals such as a control signal that is sent from the transmission and reception coils 212 (212a-212c) of the operating unit 202, and supplies a driving signal for each part to the angle member 218A, the image pickup device 220 and the illumination element 221 and the like.

The transmission and reception/control circuit 214B is connected to the transmission and reception coil 217a. When the tube unit 204 is connected to the inserting unit 203, the transmission and reception/control circuit 214B supplies an image pickup signal from the frequency modulation/power generating section 215 to the transmission and reception coil 217a and sends it to the transmission and reception coil 217b of the tube unit 204.

The leak detection mouth 222 is provided in the vicinity of the various conduits 203b and is configured to be capable of detecting the occurrence of a leak in any of the various conduits 203b.

Next, the internal configuration of the operating unit 202, inserting unit 203 and tube unit 204 of the endoscope 201 according to the present embodiment is described with reference to FIG. 21.

First, the internal configuration of the operating unit 202 is described.

As shown in FIG. 21, the control circuit 208 that is provided inside the operating unit 202 has a trackball movement detection part 235, a switch status change detection part 236, a status management part 237, a status holding memory 241 and a radio data communication part 243.

The trackball movement detection part 235 internally comprises the sensors 206a and 206b. After detecting through the sensors 206a and 206b that the trackball 206 was rotated by a technician, the trackball movement detection part 235 supplies the detection contents as a predetermined signal to the status management part 237.

After detecting that the trackball 206 was pressed by a technician and that the scope switches 207 were pressed or the like, the switch status change detection part 236 sends the detection contents as a predetermined signal to the status management part 237.

The status holding memory 241 is configured, for example, as a non-volatile rewritable recording part in which model information of the endoscope 201 and information specific to individual devices and the like is recorded.

The status management part 237 has an unshown CPU (central processing unit) and the like, and controls each part of the operating unit 202 and the inserting unit 203.

The status management part 237 supplies to the radio data communication part 243 and a control signal frequency modulating part 242 signals for performing control based on the status of predetermined signals that are sent from the trackball movement detection part 235 and the switch status change detection part 236.

Further, the status management part 237 receives via a frequency separation part 238 and a status signal demodulating part 239, image pickup signals of the interior of the body of the examinee that were photographed by an image pickup unit 231 that has the image pickup device 220.

The status management part 237 also receives as status signals the state of a sensing unit 233 and a motion controlling unit 234 that are provided in the inserting unit 203. The status management part 237 then sends a signal for carrying out control based on the state of this signal and the contents of information stored in the status holding memory 241 to the radio data communication part 243 and the control signal frequency modulating part 242. The radio data communication part 243 sends the control signal received from the status management part 237 to the antenna 211.

The frequency separation part 238 comprising the frequency modulation/power generating section 210 obtains the original power signal, status signal, image pickup signal and control signal by frequency separation processing from the synthesized signal that was received by the transmission and reception coils 212, and supplies the power signal to the power generating part 240 and the status signal, the image pickup signal and the control signal to the status signal demodulating part 239.

The status signal demodulating part 239 comprising the transmission and reception/control circuit 209 demodulates the received status signal and supplies the status signal after demodulation to the status management part 237. When an image pickup signal and a control signal are included in the synthesized signal, the status signal demodulating part 239 performs demodulation of the image pickup signal and demodulation of the control signal and supplies the post-demodulation image pickup signal and post-demodulation control signal to the status management part 237.

The power generating part 240 converts the supplied power signal into direct-current power, and supplies the power to each part of the operating unit 202. The configuration is described in detail later.

The control signal frequency modulating part 242 that comprises the transmission and reception/control circuit 209 modulates the control signal that was supplied from the status management part 237 and supplies the control signal after modulation to the transmission and reception coils 212 to send to the transmission and reception coils 213 of the inserting unit 203.

Next, the internal configuration of the inserting unit 203 will be described.

The frequency modulation/power generating section 215 provided inside the inserting unit 203 has a power current frequency modulating part 223 and a power generating part 224.

The power current frequency modulating part 223 supplies a power signal that was received by the transmission and reception coil 216a to the power generating part 224 and, in order to send the power signal to the operating unit 202, also performs modulation of the power signal and supplies the power signal after modulation to a frequency synthesizing part 225.

The power generating part 224 converts the power signal that was supplied through the power current frequency modulating part 223 into direct-current power, and supplies the power to each part of the inserting unit 203.

The status signal frequency modulating part 226 carries out modulation of a control signal that was supplied from a status signal synthesizing part 229, described later, and supplies the control signal after modulation to the frequency synthesizing part 225.

The frequency synthesizing part 225 that comprises the transmission and reception/control circuit 214A obtains a synthesized signal by performing synthesis processing of a power signal after modulation from the power current frequency modulating part 223 and a control signal after modulation from the status signal frequency modulating part 226, and supplies this synthesized signal to the transmission and reception coils 213 to be sent to the transmission and reception coils 212 of the operating unit 202.

The image pickup signal frequency modulating part 227 modulates image pickup signals that are supplied from the image pickup unit 231 that is described later, and supplies image pickup signals after modulation to the transmission and reception coil 217a to be sent to the transmission and reception coil 217b of the tube unit 204.

The control signal demodulating part 228 comprising the transmission and reception/control circuit 214A demodulates control signals supplied from the transmission and reception coils 213, and supplies the control signals after demodulation to the identification information memory 230, the image pickup unit 231 and the illumination unit 232.

The identification information memory 230 is configured, for example, as a non-volatile rewritable recording part in which model information of the endoscope 201 and information specific to individual devices and the like is recorded. Further, the identification information memory 230 supplies, to the status signal synthesizing part 229, a predetermined signal that is based on information stored in the identification information memory 230 and on the status of a control signal supplied from the control signal demodulating part 228.

The status signal synthesizing part 229 synthesizes the predetermined signal that was sent from the identification information memory 230, a status signal that was sent from the sensing unit 233, a status signal that was sent from the motion controlling unit 234, and a status signal that was sent from the image pickup unit 231, and supplies the status signal after synthesis to the status signal frequency modulating part 226. This status signal is modulated by the status signal frequency modulating part 226 as described above, and thereafter is synthesized with a power signal modulated by the frequency synthesizing part 225 and sent to the operating unit 202.

Next, the specific configuration of the image pickup unit 231, the illumination unit 232, the sensing unit 233 and the motion controlling unit 234 of the inserting unit 203 will be described.

As shown in FIG. 22, the image pickup unit 231 as an image pickup part has an image pickup device (CCD) 220, a CCD driving part 250, an amplification factor control part 251 and an ADC 252.

After receiving a control signal, i.e. an image pickup control signal, that was supplied from the control signal demodulating part 228, the CCD driving part 250 supplies an image pickup control signal to the image pickup device 220, the amplification factor control part 251 and the ADC 252.

The CCD driving part 250 then drives each part to which it has sent an image pickup control signal, based on the state of the image pickup control signal. The amplification factor control part 251 supplies the control signal that was sent from the CCD driving part 250, that is, the amplification factor control signal, to the image pickup device 220. Based on the state of the image pickup control signal and the amplification factor control signal, the image pickup device 220 performs photographing inside the body of the examinee. The images that were captured inside the body of the examinee are supplied to the ADC 252.

Upon receiving the images of the interior of the examinee's body, the ADC 252 converts the images of the interior of the examinee's body to digital signals and supplies these signals, i.e. image pickup signals, to the image pickup signal frequency modulating part 227. Further, the amplification factor control part 251 converts the amplification factor control signal to a digital signal and supplies the signal to the status signal synthesizing part 229.

As shown in FIG. 23, the illumination unit 232 has an illumination element (LED) 221 and an LED driving part 253.

The LED driving part 253 supplies a control signal that was supplied from the control signal demodulating part 228, that is, an illumination control signal (control signal that controls brightness), and status signals supplied from the status signal synthesizing part 229, that is, status signals of various units, to the illumination element 221 to drive the illumination element 221.

As shown in FIG. 24, the sensing unit 233 has contact sensors 254a, an ADC (A/D converter) 255a, a transparency sensor 254b, and an ADC 255b.

The contact sensors 254a acquire the contact pressure when the tip part of the inserting unit 203 contacts against the examinee's body, and send the acquired contact pressure value to the ADC 255a. The ADC 255a converts the contact pressure value to a digital signal, and supplies the contact pressure signal as the signal after conversion to the status signal synthesizing part 229.

The transparency sensor 254b receives reflected light that is generated by the illumination light being reflected within the examinee's body. The transparency sensor 254b determines a transparency value based on the strength of the reflected light that was received, and sends the transparency value to the ADC 255b.

The ADC 255b converts the transparency value to a digital signal, and sends a transparency signal as a post-conversion signal to the status signal synthesizing part 229.

As shown in FIG. 25, the motion controlling unit 234 has an actuator 256 comprising an encoder 256a and a bending actuator 256b, and an actuator driving part 257.

The actuator driving part 257 drives the bending actuator 256b as far as a control target position based on the state of a control signal, i.e. a target position signal that was supplied from the control signal demodulating part 228.

The encoder 256a converts the driving status of the bending actuator 256b into a digital signal, and supplies this signal, i.e. a signal indicating the present position of the bending actuator 256b to the status signal synthesizing part 229 via the actuator driving part 257.

Next, specific configurations of the power generating part 224 and the power generating part 240 that are provided in the operating unit 202 and inserting unit 203, respectively, will be described.

As shown in FIG. 26, the power generating part 224 has first to third processing circuits 260, 261 and 262. A transmitted power signal is supplied to the first to third processing circuits 260, 261 and 262.

The first processing circuit 260 has a noise filter 260a and a DC-DC converter 260b. The noise filter 260a removes a noise component in a predetermined region of a power signal, and supplies the power signal to the DC-DC converter 260b.

The DC-DC converter 260b converts the supplied power signal to direct-current power, and outputs the converted direct-current power to an unshown power supply line for a radio circuit.

The second processing circuit 261 likewise has a noise filter 261a and a DC-DC converter 261b. The noise filter 261a removes a noise component in a predetermined region of a power signal, and supplies the power signal to the DC-DC converter 261b.

The DC-DC converter 261b converts the supplied power signal to direct-current power, and outputs the converted direct-current power to an unshown power supply line for a control circuit.

The third processing circuit 262 has a noise filter 262a and a DC-DC converter 262b. The noise filter 262a removes a noise component in a predetermined region of a power signal, and supplies the power signal to the DC-DC converter 262b.

The DC-DC converter 262b converts the supplied power signal to direct-current power, and outputs the converted direct-current power to an unshown power supply line for a drive circuit.

The power generating part 240 provided in the operating unit 202 has substantially the same configuration as that of the above described power generating part 224.

By providing a noise filter for each of the circuit systems that have different operating frequencies in this manner, it is possible to prevent interference and stabilize the power supply of each circuit system.

As described above, the inserting unit 203 and the operating unit 202 of the endoscope 201 of this embodiment are attachable/detachable with respect to each other, and even when an inserting unit 203 that is of the optimal specifications for a patient is connected to the operating unit 202, driving control of an image pickup device or the like can be performed on the operating unit 202 side based on those specifications. Further, the endoscope 201 can supply power required for driving that was supplied by the inserting unit 203 via the tube unit 204 to the operating unit 202 side in a non-contact manner.

Therefore, unlike the conventional endoscopes, it is not necessary to prepare endoscopes that all have inserting units of a desired specification, and by simply changing the specifications of only the inserting unit 203 and manufacturing those units, the inserting units can be used commonly with the operating unit 202. Thus examination costs can be reduced.

Further, since the frequency of washing the operating unit 202 can be decreased, it is possible to improve durability and thereby also contribute to reducing examination costs.

In addition, since the endoscope is configured to send and receive signals in a non-contact manner between the operating unit 202 and the inserting unit 203, it is possible to reduce external projections and depressions and thereby enhance detergency. Further, since the contact points will not deteriorate due to corrosion or the like, the electrical properties can be maintained in a stable state.

As a first modification example according to this embodiment, as shown in FIG. 27, an inserting unit 203 having a light guide 263 as a light guide part can also be connected to the operating unit 202 of an endoscope 201A.

The inserting unit 203 has an illumination optical system 221A in place of the illumination element 221. Further, in place of the signal wire 214b, the light guide 263 passes through the inside of the inserting unit 203. The illumination optical system 221A is connected to the tip part of the light guide 263. The rear anchor side of the light guide 263 and a light guide 263a that communicates with the tube unit 204 and the scope connector 205 are configured such that they communicate when the tube unit 204 is connected to the inserting unit 203. As a result of this configuration, an illumination light from an unshown light source device passes within the scope connector 205, the tube unit 204 and the inserting unit 203 to be supplied to the illumination optical system 221A via the light guide 263a and the light guide 263, and thereafter is radiated at the examinee's body by the illumination optical system 221A.

Fourth Embodiment

Figure 28:
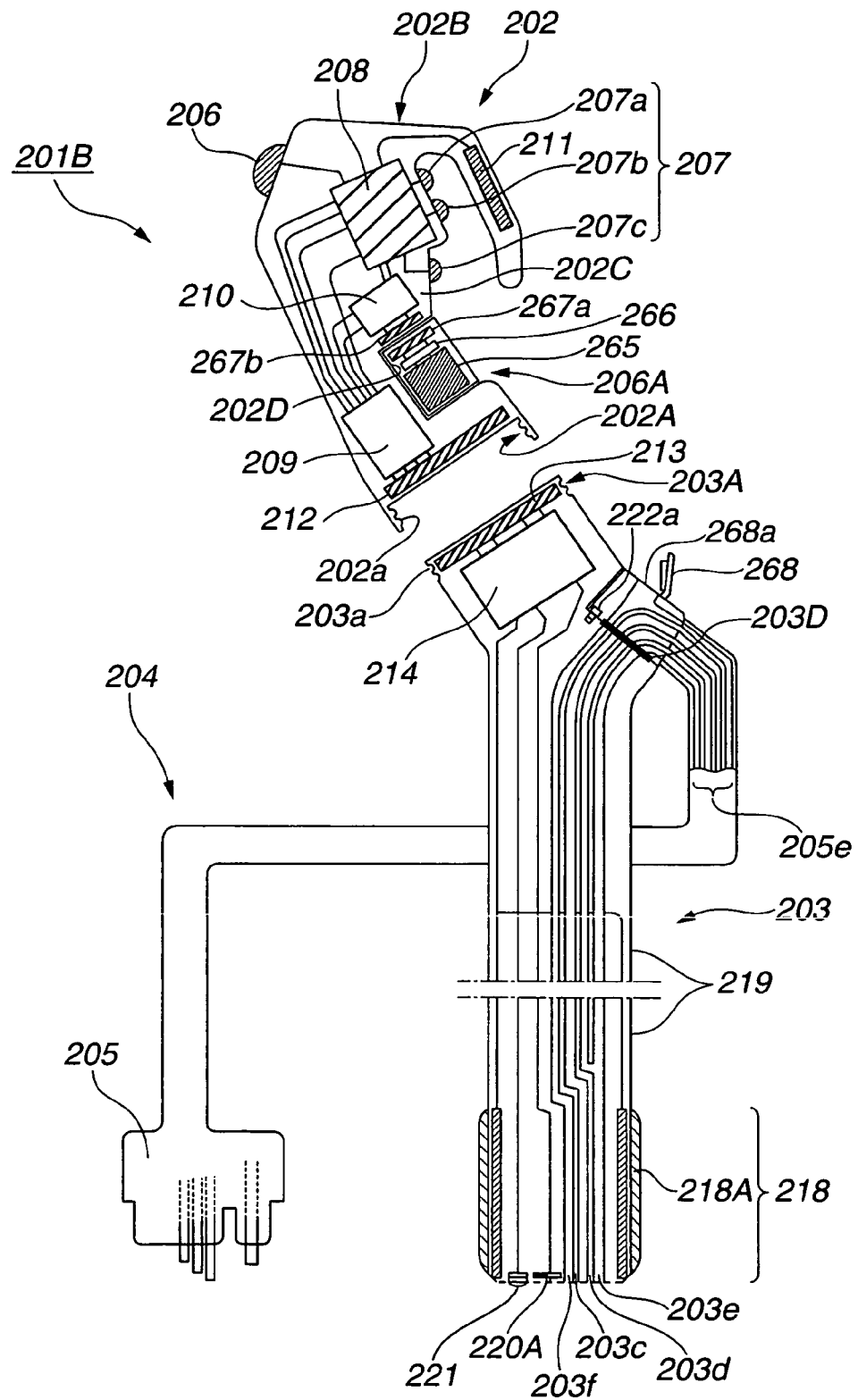
FIG. 28 is a schematic diagram showing the configuration of an endoscope according to a fourth embodiment.
Figure 29:
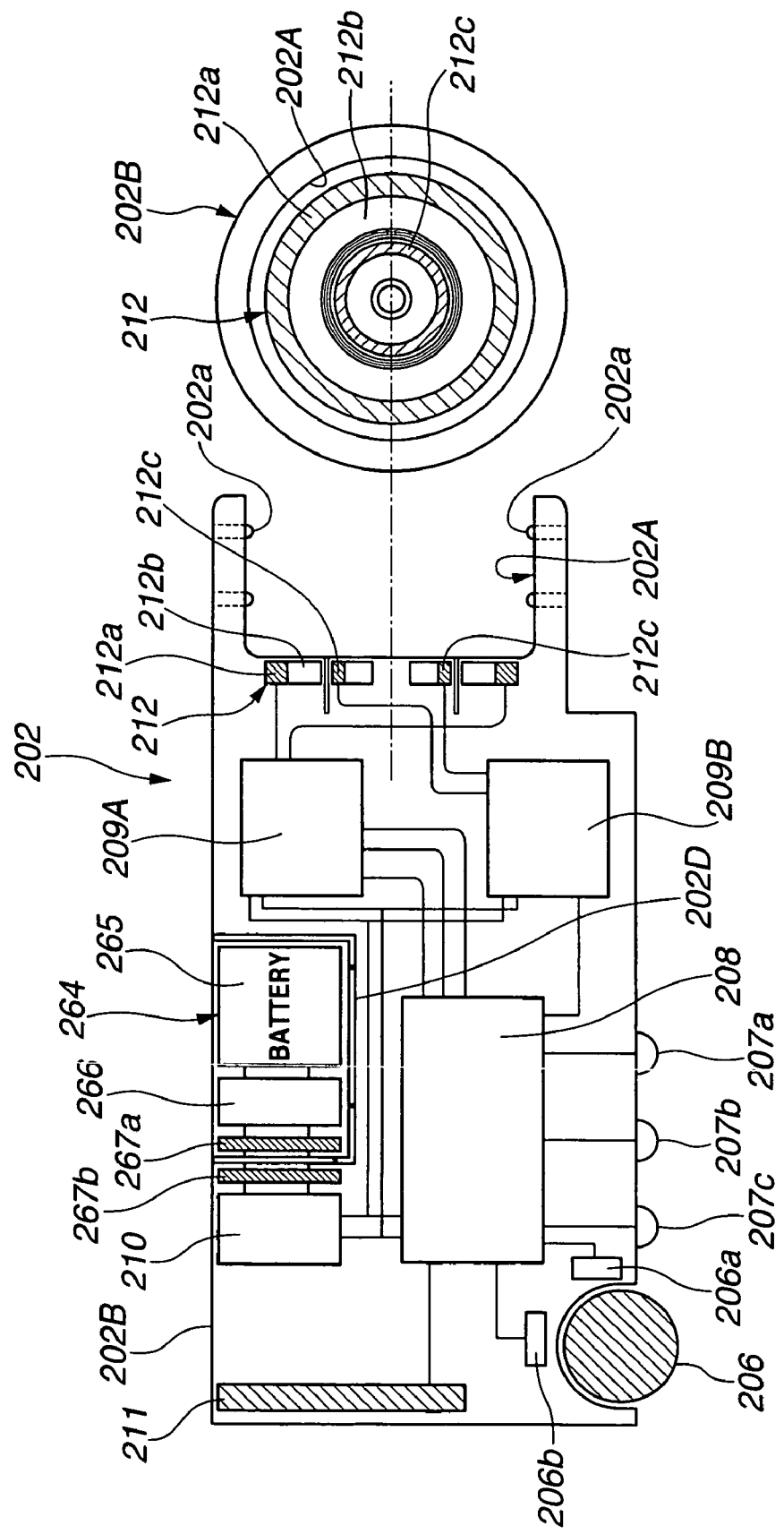
FIG. 29 is a view for describing the configuration of the operating unit shown in FIG. 28.
Figure 30:
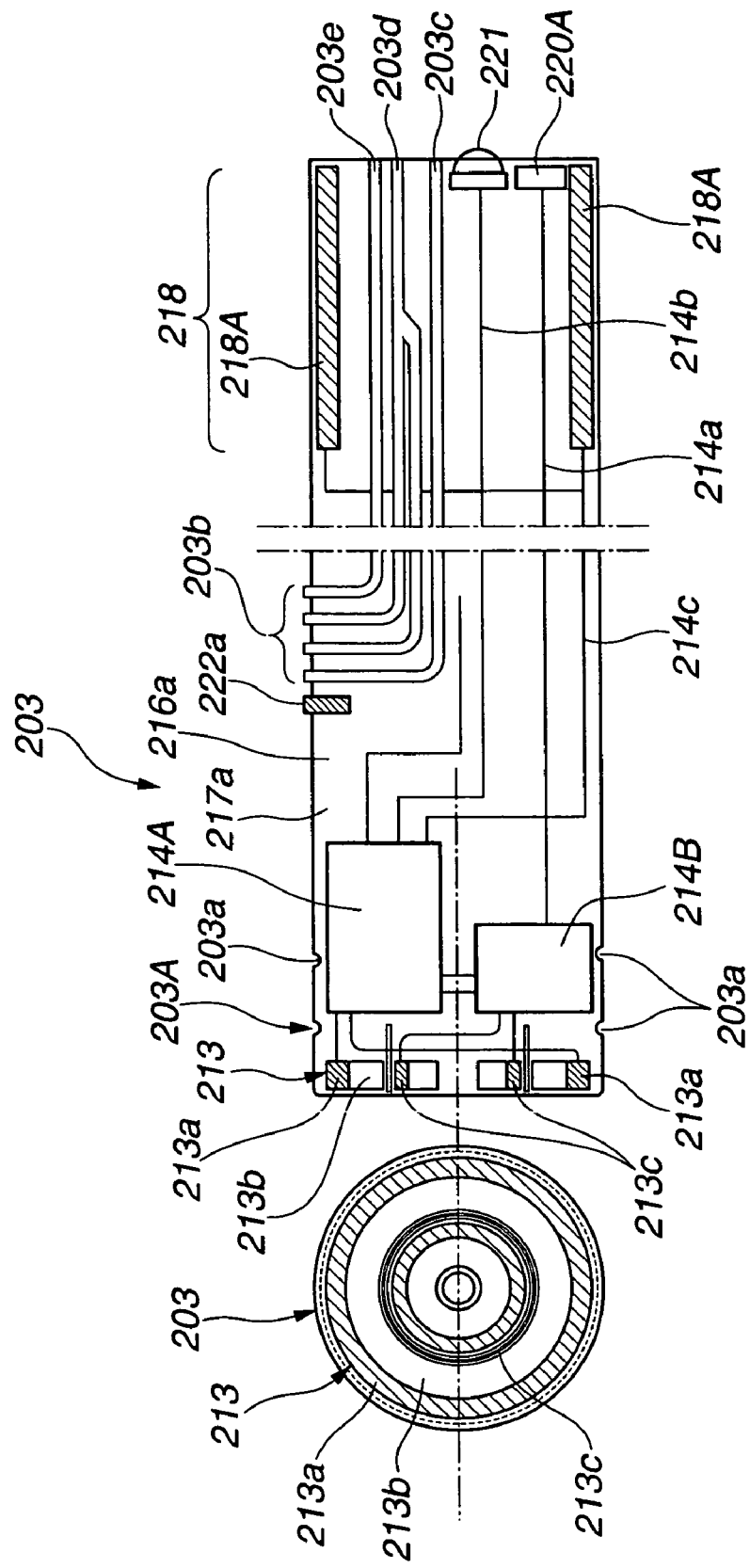
FIG. 30 is a view for describing the configuration of the inserting unit shown in FIG. 28.
Figure 31:
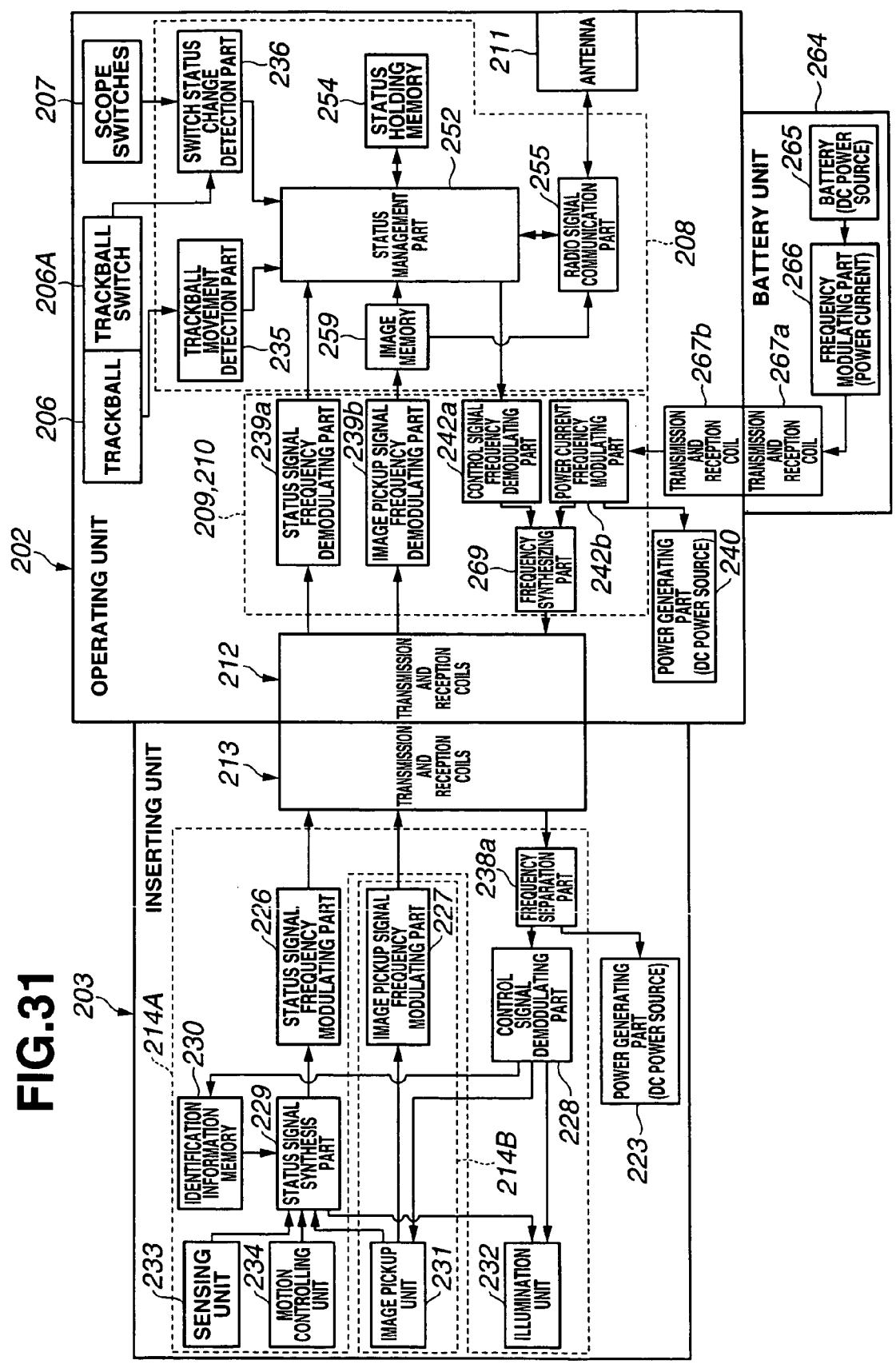
FIG. 31 is a block diagram showing the overall electrical configuration of the endoscope shown in FIG. 28.
Figure 32:
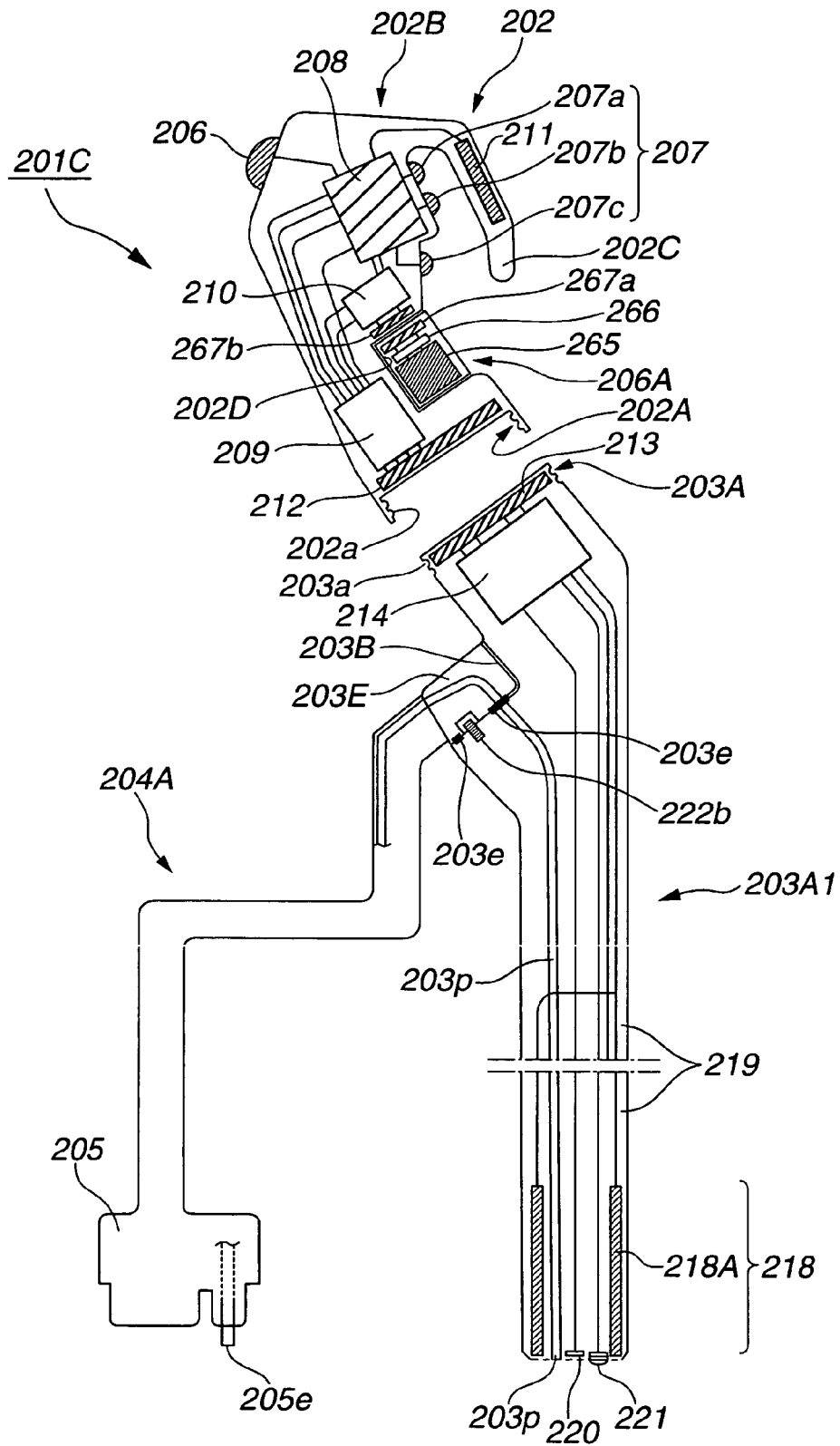
FIG. 32 is a configuration diagram for describing a first modification example of the endoscope according to the fourth embodiment.

FIGS. 28 to 32 relate to the fourth embodiment of the present invention. FIG. 28 is a schematic diagram showing the configuration of an endoscope according to the fourth embodiment. FIG. 29 is a view for describing the configuration of the operating unit shown in FIG. 28. FIG. 30 is a view for describing the configuration of the inserting unit shown in FIG. 28. FIG. 31 is a block diagram showing the overall electrical configuration of the endoscope shown in FIG. 28. FIG. 32 is a configuration diagram for describing a first modification example of the endoscope according to the fourth embodiment. Hereunder, a detailed description of portions having the same configuration as those of the first embodiment to third embodiment is omitted. Further, the same symbols are used to denote components that are the same as those in the first embodiment to third embodiments, and a description of these components is omitted.

In an endoscope 201B according to this embodiment, the method of supplying power differs from that of the endoscope 201 according to the third embodiment.

As shown in FIG. 28, the endoscope 201B according to this embodiment has an operating unit 202, an inserting unit 203 and a tube unit 204. Although the configuration of the operating unit 202 is substantially the same as that in the third embodiment, a battery unit 264 as a power supply part has a detachable connector portion 202D in the vicinity of a connector part 202A of the main body part 202B.

Further, although the inserting unit 203 is configured in substantially the same manner as in the third embodiment, it does not comprise the frequency modulation/power generating section 215. The inserting unit 203 is provided with a suction conduit 203c, an auxiliary water supply conduit 203d, an air/water supply conduit 203e, and a forceps conduit 203f. The inserting unit 203 is configured such that it is possible to detachably connect the tube unit 204 having various conduits 205e that correspond to the number of conduits of these various conduits 203c to 203f.

The battery unit 264 is configured such that a power signal can be transmitted in a non-contact manner to the operating unit 202. As shown in FIGS. 28 and 29, the battery unit 264 has a battery 265 that is the driving power, a frequency modulating part 266, and a transmission and reception coil 267a.

The battery 265 supplies a power signal to the frequency modulating part 266. The frequency modulating part 266 performs modulation in order to send the supplied power signal to the operating unit 202, and supplies the power signal after modulation to the transmission and reception coil 267a.

The transmission and reception coil 267a as a power signal transmitting part sends the power signal in a non-contact manner by electromagnetic induction to the transmission and reception coil 267b that is provided in the operating unit 202. The transmission and reception coil 267b is configured to receive the power signal in a non-contact manner by electromagnetic induction.

The transmission and reception coil 267b supplies the received power signal to the frequency modulation/power generating section 210.

When the inserting unit 203 is connected to the operating unit 202, the control circuit 208 supplies a synthesized signal of a power signal and a control signal from the frequency modulation/power generating section 210 to the transmission and reception coils 212 via the transmission and reception/control circuits 209 (209A, 209B), to send the signal to the transmission and reception coils 213 provided in the inserting unit 203.

Further, when the inserting unit 203 is connected to the operating unit 202, the control circuit 208 receives a status signal and an image pickup signal that are sent from the transmission and reception coils 213 provided in the inserting unit 203 via the transmission and reception coils 212 and the transmission and reception/control circuits 209 (209A, 209B).

As shown in FIG. 29, since, unlike the third embodiment, there is no necessity to send a power signal, the transmission and reception coils 212 comprise two transmission and reception coils 212a and 212c, and when the inserting unit 203 is connected to the operating unit 202, the transmission and reception coils 212 can send and receive various signals in a non-contact manner by electromagnetic induction from and to the transmission and reception coils 213 (213a, 213c) (see FIG. 30) that have a similar configuration.

A forceps plug 268 is provided in the vicinity of the connection with the tube unit 204 of the inserting unit 203. A forceps opening 268a that is opened by opening this forceps plug 268 communicates with the forceps conduit 203f. It is thus possible to perform treatment by inserting a treatment instrument such as a forceps through the forceps opening 268a.

Next, the internal configuration of the operating unit 202, the inserting unit 203 and the battery unit 264 of the endoscope 201 according to the present embodiment is described with reference to FIG. 31. In this connection, a description of components that are the same as those of the third embodiment is omitted, and only portions that are different from the third embodiment are described.

When the battery unit 264 is connected to the operating unit 202, a power signal that was modulated by the frequency modulating part 266 is sent to the transmission and reception coil 267b of the operating unit 202 in a non-contact manner via the transmission and reception coil 267a.

The transmission and reception coil 267b supplies the received power signal to the frequency modulation/power generating section 210.

A power current frequency modulating part 242b comprising the frequency modulation/power generating section 210 supplies the power signal that was received from the transmission and reception coil 267b to the power generating part 240, and also modulates the power signal in order to send the power signal to the inserting unit 203, and supplies the power signal after modulation to the frequency synthesizing part 269.

Similarly to the third embodiment, the power generating part 240 converts the power signal that was supplied via the power current frequency modulating part 242b into direct-current power and supplies power to each part of the inserting unit 203.

The control circuit 208 that is internally provided in the operating unit 202 also includes an image memory 259. The image memory 259 can record image pickup signals of the interior of the examinee's body that were captured by the image pickup unit 231 that has the image pickup device 220A.

The status management part 252 controls each part of the operating unit 202 and the inserting unit 203. The status management part 252 supplies the radio data communication part 243 and the control signal frequency modulating part 242a with signals for performing control and the like based on the state of predetermined signals that were supplied from the trackball movement detection part 235 and the switch status change detection part 236.

Further, the status management part 252 receives image pickup signals of the interior of the examinee's body that were captured by the image pickup unit 231 that has the image pickup device 220A, via an image pickup signal frequency demodulating part 239b and the image memory 259.

The status management part 252 also receives as status signals the status of the sensing unit 233 and the motion controlling unit 234 that are provided in the inserting unit 203. The status management part 252 then supplies signals for performing control and the like based on the state of these signals and the contents of information stored in the status holding memory 241 to the radio data communication part 243 and the control signal frequency modulating part 242a. The radio data communication part 243 sends the control signal received from the status management part 252 and an image pickup signal from the image memory to the antenna 211.

The status signal frequency demodulating part 239a that comprises the transmission and reception/control circuit 209 demodulates the received status signal, and supplies the status signal after demodulation to the status management part 252.

The image pickup signal frequency demodulating part 239d that comprises the transmission and reception/control circuit 209 demodulates the received image pickup signal, and supplies the image pickup signal after demodulation to the image memory 259.

The control signal frequency modulating part 242a that comprises the transmission and reception/control circuit 209 modulates the control signal that was sent from the status management part 252, and supplies the control signal after modulation to the frequency synthesizing part 269.

The frequency synthesizing part 269 synthesizes a power signal sent from the battery 265 to the operating unit 202 and the control signal after modulation, and sends the synthesized signal to the inserting unit 203 via the transmission and reception coils 212.

In the inserting unit 203, the status signal frequency modulating part 226 comprising the transmission and reception/ control circuit 214A modulates a control signal sent from the status signal synthesizing part 229, and sends the control signal after modulation to the status signal frequency demodulating part 239a.

The image pickup signal frequency modulating part 227 comprising the transmission and reception/control circuit 214A modulates an image pickup signal that was sent from the image pickup unit 231, and sends the image pickup signal after modulation to the image pickup signal frequency demodulating part 239b.

The control signal demodulating part 228 comprising the transmission and reception/control circuit 214A demodulates a control signal supplied from the frequency separation part 238a, and supplies the control signal after demodulation to the identification information memory 230, the image pickup unit 231 and the illumination unit 232. Further, the frequency separation part 238a separates a signal that was sent from the frequency synthesizing part 269 into a power signal and a control signal, and supplies the control signal to the control signal demodulating part 228 and the power signal to the power generating part 223. The remaining configuration is the same as that of the third embodiment.

As described above, according to this embodiment, in addition to obtaining a similar effect as that of the third embodiment, by adopting a configuration in which the battery unit 264 is attachable/detachable with respect to the operating unit 202 it is possible to supply power to the inserting unit 203 from the operating unit 202 side, and thus the number of parts of the inserting unit 203 and the tube unit 204 can be reduced. This contributes to reducing examination costs.

As a first modification example according to this embodiment, as shown in FIG. 32, a surgical flexible endoscope 203A1 can be connected to the operating unit 202 of an endoscope 201C. The surgical flexible endoscope 203A1 is configured with a smaller outer diameter than the inserting unit 203, and has various conduits 203p that include fewer conduits than the various conduits 203b of the inserting unit 203. Other than the aforementioned parts, the surgical flexible endoscope 203A1 and the inserting unit 203 have the same configuration. More specifically, the surgical flexible endoscope 203A1 has a structure that can send and receive power signals, control signals and the like in a non-contact manner, and has a dimensional shape that can be connected to a connector portion 202A of the operating unit 202.

Further, a tube unit 204A having various conduits 205e that correspond to the number of conduits of the various conduits 203p can be detachably connected to the surgical flexible endoscope 203A1. A scope connector 205 is provided at the tip part of the tube unit 204A, and has a structure that is detachable/attachable with respect to an unshown endoscope system controlling apparatus.

Fifth Embodiment

Figure 33:
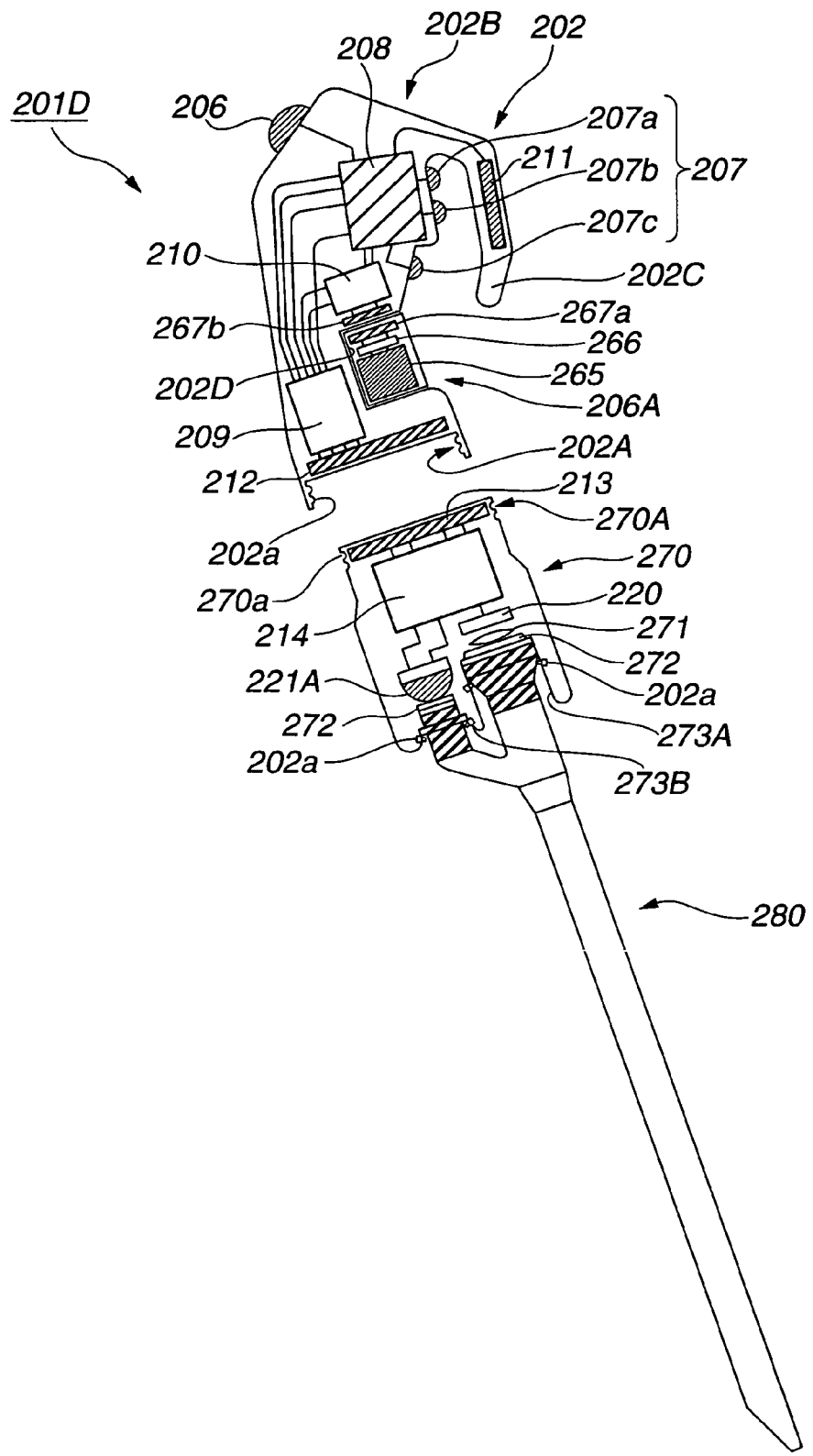
FIG. 33 is a schematic diagram showing the configuration of an endoscope according to a fifth embodiment.
Figure 34:
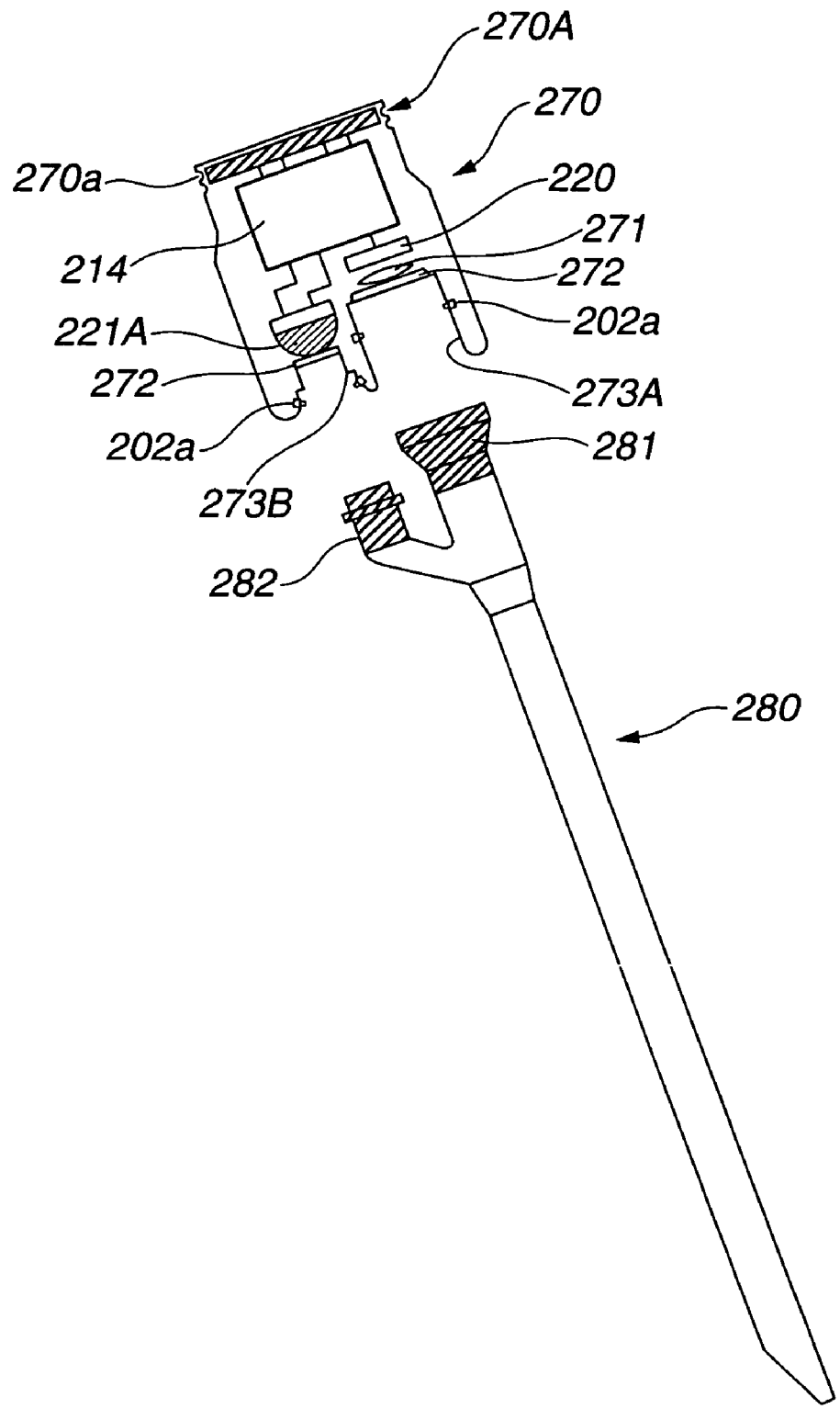
FIG. 34 is a schematic diagram for describing the configuration of a camera head adapter of the endoscope.
Figure 35:
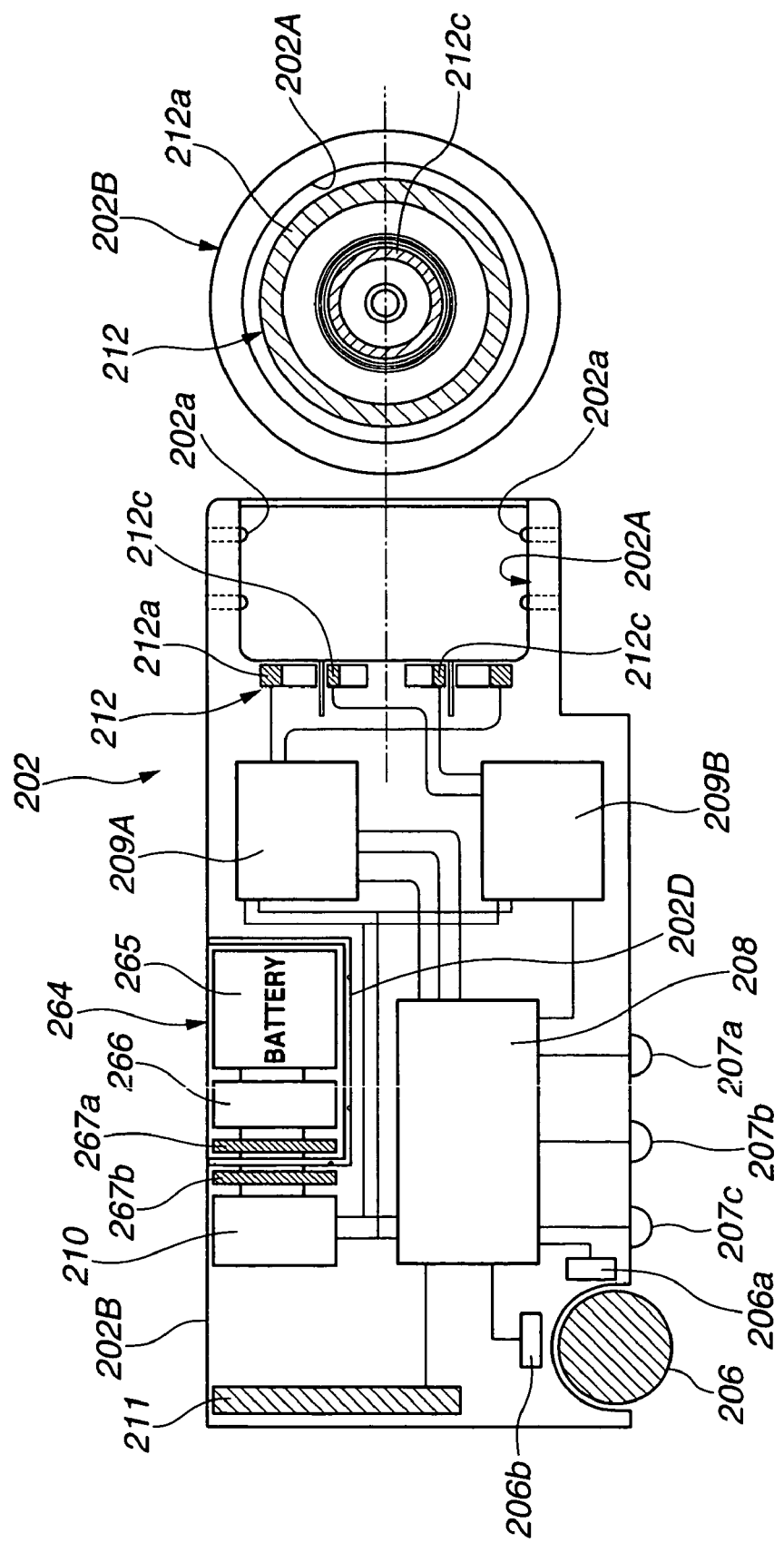
FIG. 35 is a view for describing the configuration of the operating unit shown in FIG. 33.
Figure 36:
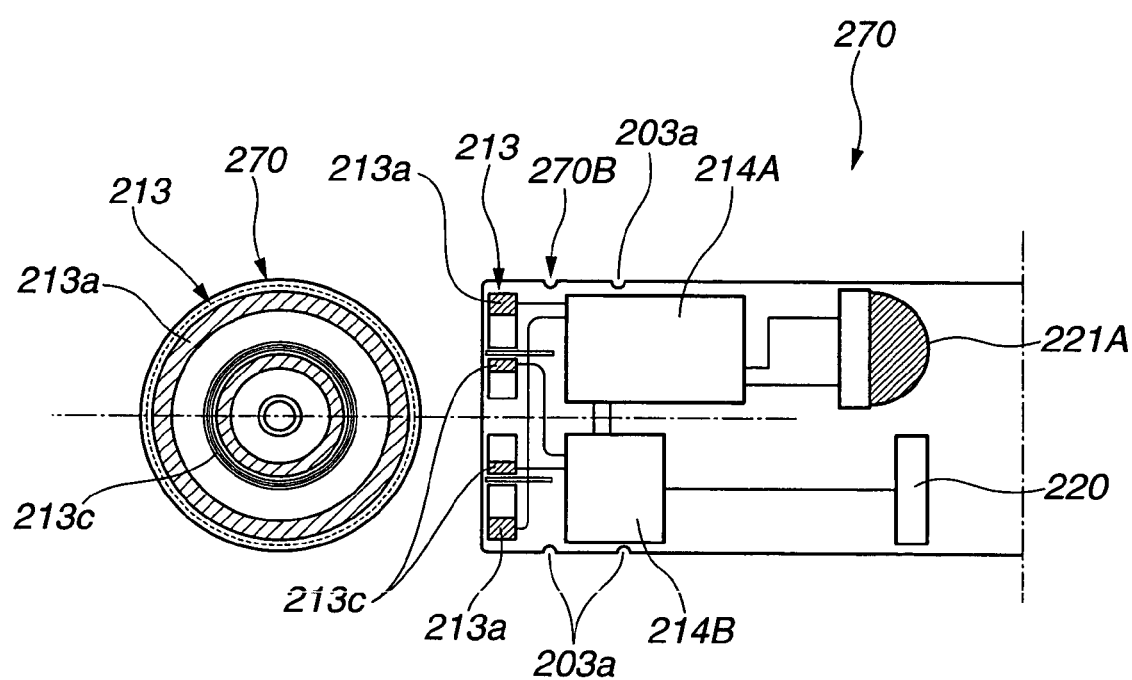
FIG. 36 is a view for describing the configuration of the camera head adapter shown in FIG. 33.
Figure 37:
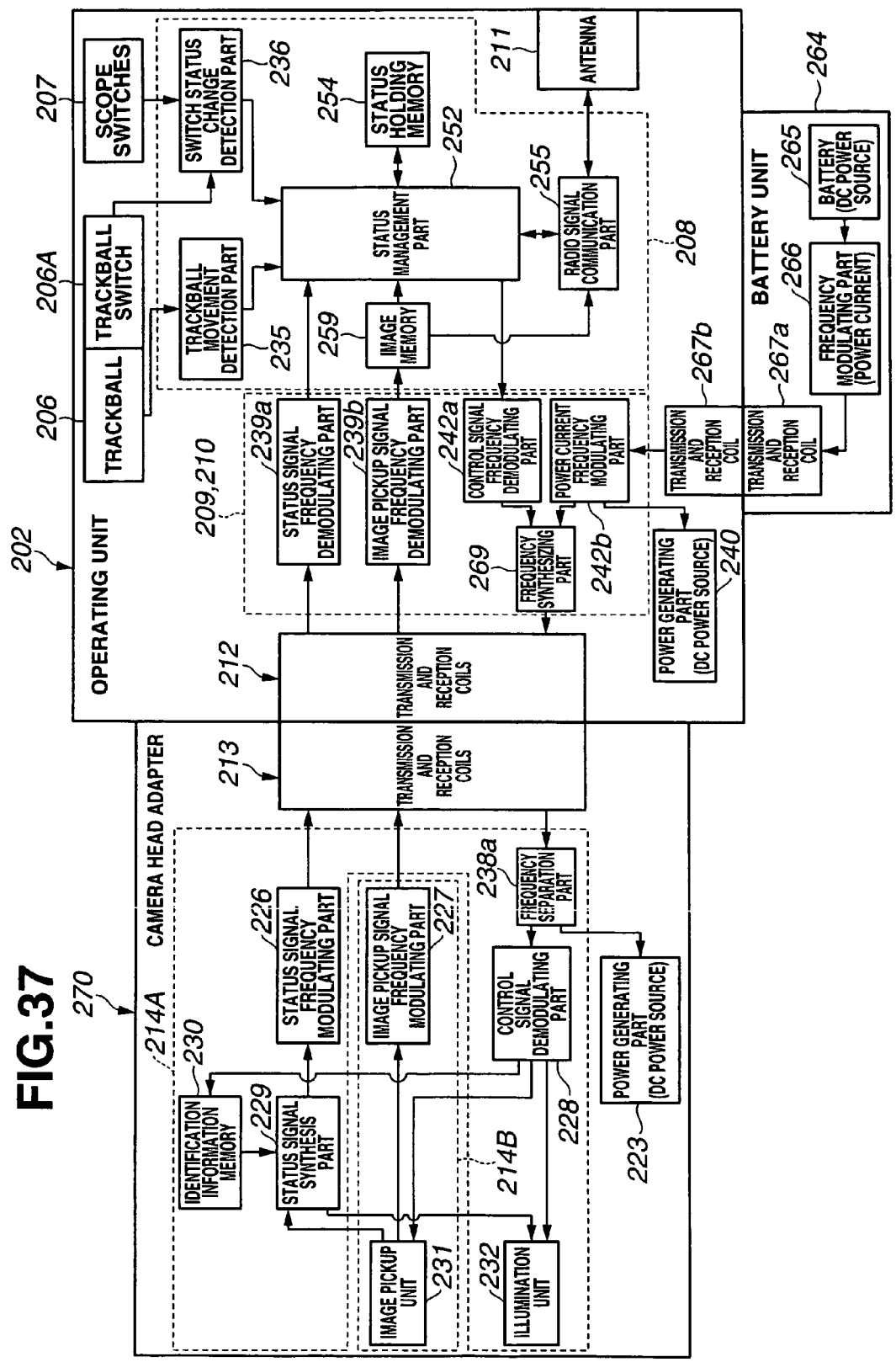
FIG. 37 is a block diagram showing the overall electrical configuration of the endoscope shown in FIG. 34.

FIGS. 33 to 37 relate to the fifth embodiment of this invention. FIG. 33 is a schematic diagram showing the configuration of an endoscope according to the fifth embodiment. FIG. 34 is a schematic diagram for describing the configuration of a camera head adapter of the endoscope. FIG. 35 is a view for describing the configuration of an operating unit shown in FIG. 33. FIG. 36 is a view for describing the configuration of the camera head adapter shown in FIG. 33. FIG. 37 is a block diagram showing the overall electrical configuration of the endoscope shown in FIG. 34. Hereunder, a detailed description of portions having the same configuration as those of the first embodiment to fourth embodiment is omitted. Further, the same symbols are used to denote components that are the same as those in the first embodiment to fourth embodiments, and a description of these components is omitted.

As shown in FIG. 33, an endoscope 201D according to this embodiment comprises an operating unit 202, a camera head adapter 270 as a connection adapter, and a rigid endoscope 280 as an inserting unit.

As shown in FIG. 35, the operating unit 202 is configured in the same manner as in the fourth embodiment and has the same components.

As shown in FIG. 33, the camera head adapter 270 is provided with peripheral grooves 270a. Ball plungers 202a of the operating unit 202 and the peripheral grooves 270a are structured such that they can engage with each other, and by means of this structure the operating unit 202 and the camera head adapter 270 are attachable/detachable and rotatable with respect to each other.

As shown in FIGS. 33 and 34, the camera head adapter 270 has two connector portions 273A and 273B that have ball plungers 202a provided on the inner peripheral surfaces as fixing members. The rigid endoscope 280 is configured in a pipe shape that has a bifurcated rear anchor part. The ball plungers 202a that are provided on the connector portions 273A and 273B, respectively, and the rear anchor parts of the rigid endoscope 280 are configured such that they can engage with each other. Thus, as shown in FIG. 34, through this configuration the camera head adapter 270 and the rigid endoscope 280 are attachable/detachable with respect to each other.

As shown in FIG. 34 and FIG. 36, the camera head adapter 270 internally comprises transmission and reception coils 213 (213a, 213c), transmission and reception/control circuits 214 (214A, 214B), an image pickup device 220, an illumination element 221A, a lens 271 and two cover glasses 272.

The lens 271 is provided in a position on the image pickup device 220 at which an image of the interior of the body of an examinee can be formed.

One of the cover glasses 272 is provided to protect the lens 271, and is disposed near a position that connects to a rear anchor part of the rigid endoscope 280 as a contact surface of the connector portion 273A. The other cover glass 272 is provided to protect the illumination element 221A, and is disposed near a position that connects to a rear anchor part of the rigid endoscope 280 as a contact surface of the connector portion 273B.

Similarly to the fourth embodiment, since the sectional form of the transmission and reception coils 213 (213a, 213c) is annular, when the camera head adapter 270 is connected to the operating unit 202, sending and receiving of various signals can be performed in a non-contact manner by electromagnetic induction with the transmission and reception coils 212 (212a and 212c) that have a similar structure.

The power required to drive each part provided in the operating unit 202 and the camera head adapter 270 is supplied to the operating unit 202 and the camera head adapter 270 as a power signal that was encoded at the battery unit 264, as in the fourth embodiment.

More specifically, a power signal that was sent from the battery unit 264 is, as shown in FIG. 35, sent in a non-contact manner to the transmission and reception coil 267b from the transmission and reception coil 267a, and thereafter is supplied to the transmission and reception coils 212 via the frequency modulation/power generating section 10 in a similar manner to the second embodiment. The transmission and reception coils 212 send the power signal in a non-contact manner by electromagnetic induction to the transmission and reception coils 213 of the camera head adapter 270. The transmission and reception coils 213 receive the power signal in a non-contact manner by electromagnetic induction.

As shown in FIG. 37, the internal configuration of the endoscope 201D according to this embodiment is substantially the same as the configuration described in the fourth embodiment, with the camera head adapter 270 being provided in place of the inserting unit 203. In this case, since the rigid endoscope 280 is attached to the camera head adapter 270, the sensing unit 233 and motion controlling unit 234 shown in FIG. 31 are not provided.

The endoscope 201D according to this embodiment functions in substantially the same manner as the endoscope 201B according to the fourth embodiment.

Therefore, according to this embodiment, in addition to obtaining the same effect as that of the fourth embodiment, the rigid endoscope 280 that is used in particular in an operating room can be connected to the operating unit 202, and furthermore, since power can be supplied from the battery unit 264, it is possible to eliminate the plurality of connection cables that are connected to the conventional rigid endoscope. It is thus possible to enhance the operability of the endoscope and to reduce examination costs.

Further, since the endoscope 201D can be used in a wireless manner that does not require connection cables, when a plurality of endoscopes 201D are provided, it is also possible to connect to a network such as a LAN inside the hospital or operating room to facilitate more effective performance of an operation.

The present invention is not limited to the first to the fifth embodiments and the modification examples, and various changes and modifications and the like are possible without departing from the spirit and scope of the present invention.

What is claimed is:

1. An endoscope comprising:
   an operating unit that at least actuates a function of an endoscope;
   an inserting unit that is detachably connected to the operating unit;
   a first signal transmission and reception section that is provided to the operating unit; and
   a second signal transmission and reception section that is provided to the inserting unit;
   wherein the inserting unit comprises an image pickup part and a drive control part that controls the image pickup part, and the operating art that controls the drive control part based on a signal that is output from the drive control part,
   the endoscope further comprising,
   a tube unit that is provided with conduits that communicate with a plurality of conduits inside the inserting unit and a signal wire that connects to the drive control part when the tube unit is connected to the inserting unit,
   wherein, when the operating unit and the inserting unit are connected, the first signal transmission and reception section and the second signal transmission and reception section are disposed apart from each other.

2. The endoscope according to claim 1, further comprising:
   an operating unit side engaging portion that is provided to the operating unit; and
   an inserting unit side engaging portion that is provided to the inserting unit and has a structure that is attachable/detachable with respect to the operating unit side engaging portion,
   wherein, when the operating unit side engaging portion and the inserting unit side engaging portion are connected, the first signal transmission and reception section and the second signal transmission and reception section are disposed apart from each other.

3. The endoscope according to claim 2, wherein the operating unit side engaging portion has a connector portion that is formed at an end of the operating unit, and protrusions that are provided on an inner peripheral surface of the connector portion, and the inserting unit side engaging portion has concave portions that are provided on an outer peripheral surface of the inserting unit and are configured to be capable of engaging with the protrusions.

4. The endoscope according to claim 1, wherein the inserting unit further comprises a power generating part that generates power to be utilized in the inserting unit, and the first signal transmission and reception section sends a power signal that is based on the power to the second signal transmission and reception section, and the second signal transmission and reception section sends the received power signal to the power generating part.

5. The endoscope according to claim 1, wherein the operating unit and the inserting unit further internally comprise a first light guide part and a second light guide part, respectively, and when the inserting unit is connected to the operating unit, the first light guide part and the second light guide part communicate.

6. The endoscope according to claim 1, wherein the tube unit sends a power signal from a power source to the drive unit control part through the signal wire, and the drive control part sends the received power signal to the control part through the signal transmission and reception sections.

7. The endoscope according to claim 1, wherein the operating unit further comprises a power supply part that is configured to be attachable/detachable with respect to the operating unit, and the power supply part sends a power signal to the control part through a power signal sending part that sends a power signal in a non-contact manner between the operating unit and the power supply part, and the control part sends the received power signal to the drive control part through the signal transmission and reception sections.

8. An endoscope comprising:
   an operating unit that at least actuates a function of an endoscope;
   an inserting unit that is detachably connected to the operating unit;
   a first signal transmission and reception section that is provided to the operating unit; and
   a second signal transmission and reception section that is provided to the inserting unit;
   wherein the inserting unit comprises an image pickup part and a drive control part that controls the image pickup part, and the operating unit has a control part that controls the drive control part based on a signal that is output from the drive control part,
   the endoscope further comprising,
   a tube unit that is provided with conduits that communicate with a plurality of conduits inside the inserting unit and a signal wire that connects to the drive control part when the tube unit is connected to the inserting unit,
   wherein, when the operating unit and the inserting unit are connected, the first signal transmission and reception section and the second signal transmission and reception section perform sending and receiving of signals between the operating unit and the inserting unit in a non-contact manner.

9. The endoscope according to claim 8, further comprising:
   an operating unit side engaging portion that is provided to the operating unit;

an inserting unit side engaging portion that is provided to the inserting unit and has a structure that is attachable/detachable with respect to the operating unit side engaging portion;

wherein, when the operating unit side engaging portion and the inserting unit side engaging portion are connected, the first signal transmission and reception section and the second signal transmission and reception section perform sending and receiving of signals between the operating unit and the inserting unit in a non-contact manner.

10. The endoscope according to claim 9, wherein the operating unit side engaging portion has a connector portion that is formed at an end of the operating unit, and protrusions that are provided on an inner peripheral surface of the connector portion, and the inserting unit side engaging portion has concave portions that are provided on an outer peripheral surface of the inserting unit and are configured to be capable of engaging with the protrusions.

11. The endoscope according to claim 8, wherein the inserting unit further comprises a power generating part that generates power to be utilized in the inserting unit, and the first signal transmission and reception section sends a power signal that is based on the power to the second signal transmission and reception section, and the second signal transmission and reception section sends the received power signal to the power generating part.

12. The endoscope according to claim 8,
wherein the operating unit and the inserting unit further internally comprise a first light guide part and a second light guide part, respectively; and
when the inserting unit is connected to the operating unit, the first light guide part and the second light guide part communicate.

13. The endoscope according to claim 8, wherein the tube unit sends a power signal from a power source to the drive control part through the signal wire, and the drive control part sends the received power signal to the control part through the signal transmission and reception sections.

14. The endoscope according to claim 8, wherein the operating unit further comprises a power supply part that is configured to be attachable/detachable with respect to the operating unit, and the power supply part sends a power signal to the control part through a power signal sending part that sends a power signal in a non-contact manner between the operating unit and the power supply part, and the control part sends the received power signal to the drive control part through the signal transmission and reception sections.

15. An endoscope, comprising:
an operating unit that at least actuates a function of an endoscope;
an inserting unit that is detachably connected to the operating unit;
a first signal transmission and reception section that is provided to the operating unit; and
a second signal transmission and reception section that is provided to the inserting unit;
wherein the inserting unit comprises an image pickup part and a drive control part that controls the image pickup part, the operating unit comprises a control part that controls the drive control part based on a signal that is output from the drive control part and a power supply part that is configured to be attachable/detachable with respect to the operating unit, the power supply part sends a power signal to the control part through a power signal sending part that sends a power signal in a non-contact manner between the operating unit and the power supply part, and the control part sends the received power signal to the drive control part through the signal transmission and reception sections,
wherein, when the operating unit and the inserting unit are connected, the first signal transmission and reception section and the second signal transmission and reception section are disposed apart from each other.

16. An endoscope comprising:
an operating unit that at least actuates a function of an endoscope;
an inserting unit that is detachably connected to the operating unit;
a first signal transmission and reception section that is provided to the operating unit; and
a second signal transmission and reception section that is provided to the inserting unit,
wherein the inserting unit comprises an image pickup part and a drive control part that controls the image pickup part, the operating unit comprises a control part that controls the drive control part based on a signal that is output from the drive control part and a power supply part that is configured to be attachable/detachable with respect to the operating unit, the power supply part sends a power signal to the control part through a power signal sending part that sends a power signal in a non-contact manner between the operating unit and the power supply part, and the control part sends the received power signal to the drive control part through the signal transmission and reception sections,
wherein, when the operating unit and the inserting unit are connected, the first signal transmission and reception section and the second signal transmission and reception section perform sending and receiving of signals between the operating unit and the inserting unit in a non-contact manner.

17. An endoscope comprising:
an operating unit that at least actuates a function of an endoscope;
an inserting unit;
a connection adapter that is attachable/detachable with respect to the operating unit, and connects the inserting unit to the operating unit;
a first signal transmission and reception section that is provided to the inserting unit; and
a second signal transmission and reception section that is provided to the connection adapter;
wherein the connection adapter comprises an image pickup part and a drive control part that controls the image pickup part, the operating unit comprises a control part that controls the drive control part based on a signal that is output from the drive control part and a power supply part that is configured to be attachable/detachable with respect to the operating unit, the power supply part sends a power signal to the control part through a power signal sending part that sends a power signal in a non-contact manner between the operating unit and the power supply part, and the control part sends the received power signal to the drive control part through the signal transmission and reception sections,
wherein, when the operating unit and the connection adapter are connected, the first signal transmission and reception section and the second signal transmission and reception section are disposed apart from each other.

18. The endoscope according to claim 17, further comprising:
an operating unit side engaging portion that is provided to the operating unit;

a connection adapter side engaging portion that is provided to the connection adapter and has a structure that is attachable/detachable with respect to the operating unit side engaging portion;

wherein, when the operating unit side engaging portion and the connection adapter side engaging portion are connected, the first signal transmission and reception section and the second signal transmission and reception section are disposed apart from each other.

19. The endoscope according to claim 18, wherein the operating unit side engaging portion has a connector portion that is formed at an end of the operating unit, and protrusions that are provided on an inner peripheral surface of the connector portion, and the connection adapter side engaging portion has concave portions that are provided on an outer peripheral surface of the connection adapter and are configured to be capable of engaging with the protrusions.

20. The endoscope according to claim 17, wherein the connection adapter comprises a power generating part that generates power to be utilized in the connection adapter, and the first signal transmission and reception section sends a power signal that is based on the power to the second signal transmission and reception section, and the second signal transmission and reception section sends the received power signal to the power generating part.

21. The endoscope according to claim 17, wherein the operating unit and the connection adapter further internally comprise a third light guide part and a fourth light guide part, respectively, and when the connection adapter is connected to the operating unit, the third light guide part and the fourth light guide part communicate.

22. An endoscope comprising:
an operating unit that at least actuates a function of an endoscope;
an inserting unit;
a connection adapter that is attachable/detachable with respect to the operating unit, and connects the inserting unit to the operating unit;
a first signal transmission and reception section that is provided to the operating unit; and
a second signal transmission and reception section that is provided to the connection adapter,
wherein the connection adapter comprises an image pickup part and a drive control part that controls the image pickup part, the operating unit comprises a control part that controls the drive control part based on a signal that is output from the drive control part and a power supply part that is configured to be attachable/detachable with respect to the operating unit, the power supply part sends a power signal to the control part through a power signal sending part that sends a power signal in a non-contact manner between the operating unit and the power supply part, and the control part sends the received power signal to the drive control part through the signal transmission and reception section, wherein, when the operating unit and the connection adapter are connected, the first signal transmission and reception section and the second signal transmission and reception section perform sending and receiving of signals between the inserting unit and the connection adapter in a non-contact manner.

23. The endoscope according to claim 22, further comprising:
an operating unit side engaging portion that is provided to the operating unit;
a connection adapter side engaging portion that is provided to the connection adapter and has a structure that is attachable/detachable with respect to the operating unit side engaging portion,
wherein, when the operating unit side engaging portion and the connection adapter side engaging portion are connected, the first signal transmission and reception section and the second signal transmission and reception section perform sending and receiving of signals between the inserting unit and the connection adapter in a non-contact manner.

24. The endoscope according to claim 23, wherein the operating unit side engaging portion has a connector portion that is formed at an end of the operating unit, and protrusions that are provided on an inner peripheral surface of the connector portion, and the connection adapter side engaging portion has concave portions that are provided on an outer peripheral surface of the connection adapter and are configured to be capable of engaging with the protrusions.

25. The endoscope according to claim 22,
wherein the connection adapter further comprises a power generating part that generates power to be utilized in the connection adapter, and the first signal transmission and reception section sends a power signal that is based on the power to the second signal transmission and reception section, and the second signal transmission and reception section sends the received power signal to the power generating part.

26. The endoscope according to claim 22,
wherein the operating unit and the connection adapter further internally comprise a third light guide part and a fourth light guide part, respectively, and when the connection adapter is connected to the operating unit, the third light guide part and the fourth light guide part communicate.

* * * * *

UNITED STATES PATENT AND TRADEMARK OFFICE
CERTIFICATE OF CORRECTION

| | | |
|---|---|---|
| PATENT NO. | : 7,914,443 B2 | |
| APPLICATION NO. | : 11/599562 | |
| DATED | : March 29, 2011 | |
| INVENTOR(S) | : Sumihiro Uchimura et al. | |

It is certified that error appears in the above-identified patent and that said Letters Patent is hereby corrected as shown below:

Column 27, line 45 (claim 1, line 12): should read as: part, and the operating unit has a control part that controls the drive control Signed and Sealed this
Second Day of August, 2011

David J. Kappos
*Director of the United States Patent and Trademark Office*